(12) United States Patent
Galley et al.

(10) Patent No.: US 8,158,668 B2
(45) Date of Patent: *Apr. 17, 2012

(54) METHODS FOR TREATING CNS DISORDERS WITH 4-IMIDAZOLE DERIVATIVES

(75) Inventors: Guido Galley, Rheinfelden (DE); Katrin Groebke Zbinden, Liestal (CH); Marius Hoener, Basel (CH); Roger Norcross, Olsberg (CH); Henri Stalder, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 1188 days.

This patent is subject to a terminal disclaimer.

(21) Appl. No.: 11/655,539

(22) Filed: Jan. 19, 2007

(65) Prior Publication Data

US 2007/0197622 A1 Aug. 23, 2007

(30) Foreign Application Priority Data

Jan. 27, 2006 (EP) .................................... 06100938

(51) Int. Cl.
*A01N 43/50* (2006.01)
*A61K 31/415* (2006.01)
*C07D 233/00* (2006.01)

(52) U.S. Cl. ..................................... 514/397; 548/335.1
(58) Field of Classification Search .................. 514/397; 548/335.1

See application file for complete search history.

(56) References Cited

U.S. PATENT DOCUMENTS

| 3,956,426 A | 5/1976 | Schepers |
| 4,443,466 A * | 4/1984 | Karjalainen et al. .......... 514/396 |
| 7,078,401 B2 * | 7/2006 | Bley et al. .................. 514/235.8 |
| 2003/0181354 A1 | 9/2003 | Abdulrazik |
| 2003/0236274 A1 | 12/2003 | Tasaka et al. |

FOREIGN PATENT DOCUMENTS

| EP | 0 024 829 A1 | 3/1981 |
| EP | 0 331 374 A2 | 9/1989 |
| EP | 0 424 059 A1 | 4/1991 |
| EP | 1 413 576 A2 | 4/2004 |
| JP | 63-150224 | 6/1988 |
| WO | 92/21334 | 12/1992 |
| WO | 97/15302 | 5/1997 |
| WO | 01/30762 | 5/2001 |
| WO | WO 01/30762 A1 | 5/2001 |
| WO | 2005/034998 | 4/2005 |
| WO | WO 2006036480 A1 * | 4/2006 |

OTHER PUBLICATIONS

Cossement, E. et al. "Mivazerol and other benzylimidazoles with alpha-2 adrenergiques" Journal de pharmacie de belgique, May 1994, vol. 49, issue 3, pp. 206-215.*
Stoilov, I. et al. "Synthesis of Detomindine and Medetomidine metabolites: 1,2,3-trisubstituted arenes with 4'(5')-Imidazolylmethyl Groups" J. Hetercyclic Chem., Dec. 1993, vol. 30, pp. 1645-1651.*
Clark et al. "Discovery and SAR development of 2-(phenylamino)imidazolines as postacyclin receptor antagonists" Bioorg. Med. Chem. Lett., Feb. 2004, pp. 1053-1056.*
Hong et al. "A Structure-Activity Relationship Study of Benzylic Modifications of 4-[1-(1-Naphthypethyl]-1H-imidazoles on alpha1- and alpha2-Adrenergic Receptors" J. Med.Chem., 1994, vol. 37, pp. 2328-2333.*
Miller et al. "Optically Active Catecholimidzolines: A Study of Steric Interactions at alpha-Adrenoreceptors" J. Med.Chem.,1983, vol. 26, pp. 957-963.*
Deutch et al., (1999) Neurotransmitters. In Fundamental Neuroscience (2$^{nd}$ ed.) pp. 193-234, Academic Press.
Wong, et al., (2001) Nat. Rev. Neurosci. 2, pp. 343-351.
Carlsson et al., (2001) Annu. Rev. Pharmacol. Toxicol. 41, pp. 237-260.
Tuite et al., (2003) Expert Opin. Investig. Drugs 12, pp. 1335-1352.
Castellanos et al., (2002) Nat. Rev. Neurosci. 3, pp. 617-628.
Usdin, E. and Sandler. M.; Editors. Psychopharmacology Series, vol. 1: Trace Amines and the Brain. [Proceedings of a Study Group at the 14th Annual Meeting of the American College of Neuropsychoparmacology, San Juan, Puerto Rico] (1976) pp. 1-281.
Lindemann, et al., (2005) Trends in Pharmacol. Sci. 26, pp. 274-281.
Branchek et al., (2003) Curr. Opin. Pharmacol. 3, pp. 90-97.
Premont et al. (2001) Proc. Natl. Acad. Sci. U. S. A. 98, pp. 9474-9475.
Mosseau et al., (1995) Prog. Brain Res. 106, pp. 285-291.
McCormack et al. (1986) J. Neurosci. 6, pp. 94-101.
Dyck, L.E. (1989) Life Sci. 44, pp. 1149-1156.
Parker, et al., (1988) J. Pharmacol. Exp. Ther. 245, pp. 199-210.
Lindemann, L. et al. (2005) Genomics 85, pp. 372-385.
Turner, et al., J. Org. Chem. (1991), 56, pp. 5739-5740.

(Continued)

*Primary Examiner* — Sreeni Padmanabhan
*Assistant Examiner* — Kendra D Carter
(74) *Attorney, Agent, or Firm* — George W. Johnston; Patricia S. Rocha-Tramaloni; Kimberly J. Prior

(57) ABSTRACT

The present invention relates to methods for treating depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders which comprises administering to an individual a therapeutically effective amount of a compound of formula I

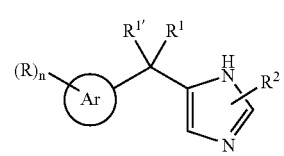

wherein
R, Ar, $R^1$, $R^{1'}$, $R^2$, and n are as defined in the specification and to their pharmaceutically active salts, racemic mixtures, enantiomers, optical isomers and tautomeric forms. The invention also relates to novel compounds of formula I, compositions containing them, and methods for their preparation.

3 Claims, No Drawings

OTHER PUBLICATIONS

Cahiez et al., Synthesis, (1999), pp. 2138-2144.
Nakamura et al., J. Chem. Soc. Perkin Trans. 1, (2002), pp. 1061-1066.
Nobuyuki Matsunaga, et al., Bioorganic & Medicinal Chemistry, p. 4314 (2004), XP002444990.
Matsunaga, N., et al., Tetrahedron: Asymmetry, Elsevier Science Publishers, vol. 15, No. 13, pp. 2021-2028 (2004), XP004520137.
Ojida, A., et al., Tetrahedron: Asymmetry, Elsevier Science Publishers, vol. 15, No. 10, pp. 1555-1559 (2004), XP004508431.
(Translation of Israeli Office Action in Corresponding Appl. No. 192885 Sep. 26, 2011).
Yoshiya Amemiya et al., Journal of Medicinal Chemistry (XP002151512), 35(4):750-755 (1992).
Ojida, A. et al., Tetrahedron Asymmetry 15:1555-1559.
(English Translation of Japanese Off Action in Corres Appl 2008-551759 Dec. 20, 2011).
Matsunaga, N. et al., tETRAHEDRON aSYMMETRY 15:2021-2028 (2004).

* cited by examiner

METHODS FOR TREATING CNS DISORDERS WITH 4-IMIDAZOLE DERIVATIVES

PRIORITY TO RELATED APPLICATIONS

This application claims the benefit of European Application No. 06100938.7, filed Jan. 27, 2006, which is hereby incorporated by reference in its entirety.

BACKGROUND OF THE INVENTION

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlap with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression [7] and for other conditions like attention deficit hyperactivity disorder, migraine headache, Parkinson's disease, substance abuse and eating disorders [8,9].

For a long time, TA-specific receptors had only been hypothesized based on anatomically discrete high-affinity TA binding sites in the CNS of humans and other mammals [10,11]. Accordingly, the pharmacological effects of TAs were believed to be mediated through the well known machinery of classical biogenic amines, by either triggering their release, inhibiting their reuptake or by "crossreacting" with their receptor systems [9,12,13]. This view changed significantly with the recent identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies [7,14]. TAAR1 is in the first subclass of four genes (TAAR1-4) highly conserved between human and rodents. TAs activate TAAR1 via Gαs. Dysregulation of TAs was shown to contribute to the aetiology of various diseases like depression, psychosis, attention deficit hyperactivity disorder, substance abuse, Parkinson's disease, migraine headache, eating disorders, metabolic disorders and therefore TAAR ligands have a high potential for the treatment of these diseases.

Therefore, there is a broad interest to increase the knowledge about trace amine associated receptors.

SUMMARY OF THE INVENTION

The present invention provides a method for treating a disorder selected from the group consisting of depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders which comprises administering to an individual a therapeutically effective amount of a compound of formula I

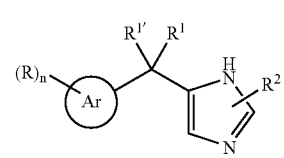

wherein
R is hydrogen,
  halogen,
  lower alkyl,
  lower alkoxy,
  hydroxy,
  phenyl,
  S-phenyl or O-phenyl, each of which is optionally substituted by lower alkoxy or halogen,
  benzyloxy,
  C(O)O-lower alkyl,
  cycloalkyl,
  lower alkyl substituted by halogen, or
  lower alkoxy substituted by halogen;
Ar is aryl or heteroaryl, selected from the group consisting of phenyl, naphthyl, pyridinyl, benzofuranyl, dihydrobenzofuranyl and pyrazolyl;
$R^1$ and $R^{1'}$ are each independently hydrogen,
  hydroxy,
  lower alkyl,
  lower alkoxy, or
  phenyl or benzyl, each of which is optionally substituted by halogen;
$R^2$ is hydrogen or lower alkyl; and
n is 1, 2, 3 or 4;
and their pharmaceutically active salts, racemic mixtures, enantiomers, optical isomers and tautomeric forms.

Compounds of formula I have a good affinity to the trace amine associated receptors (TAARs), especially for TAAR1.

The preferred indications of the present invention are depression, psychosis, Parkinson's disease, anxiety and attention deficit hyperactivity disorder (ADHD).

Some of the compounds disclosed in formula I are known compounds, described for example in the below mentioned references, or are enclosed in public chemical libraries. Compounds of examples 1-23 and 44-80 are novel.

REFERENCES USED

1 Deutch, A. Y. and Roth, R. H. (1999) Neurotransmitters. In *Fundamental Neuroscience* ($2^{nd}$ edn) (Zigmond, M. J., Bloom, F. E., Landis, S. C., Roberts, J. L, and Squire, L. R., eds.), pp. 193-234, Academic Press;
2 Wong, M. L. and Licinio, J. (2001) Research and treatment approaches to depression. *Nat. Rev. Neurosci.* 2, 343-351;
3 Carlsson, A. et al. (2001) Interactions between monoamines, glutamate, and GABA in schizophrenia: new evidence. *Annu. Rev. Pharmacol. Toxicol.* 41, 237-260;

4 Tuite, P. and Riss, J. (2003) Recent developments in the pharmacological treatment of Parkinson's disease. *Expert Opin. Investig. Drugs* 12, 1335-1352, 5 Castellanos, F. X. and Tannock, R. (2002) Neuroscience of attention-deficit/hyperactivity disorder: the search for endophenotypes. *Nat. Rev. Neurosci.* 3, 617-628;

6 Usdin, E. and Sandler, M. eds. (1984), *Trace Amines and the brain*, Dekker;

7 Lindemann, L. and Hoener, M. (2005) A renaissance in trace amines inspired by a novel GPCR family. *Trends in Pharmacol. Sci.* 26, 274-281;

8 Branchek, T. A. and Blackburn, T. P. (2003) Trace amine receptors as targets for novel therapeutics: legend, myth and fact. *Curr. Opin. Pharmacol.* 3, 90-97;

9 Premont, R. T. et al. (2001) Following the trace of elusive amines. *Proc. Natl. Acad. Sci. U.S.A.* 98, 9474-9475;

10 Mousseau, D. D. and Butterworth, R. F. (1995) A high-affinity [3H] tryptamine binding site in human brain. *Prog. Brain Res.* 106, 285-291;

11 McCormack, J. K. et al. (1986) Autoradiographic localization of tryptamine binding sites in the rat and dog central nervous system. *J. Neurosci.* 6, 94-101;

12 Dyck, L. E. (1989) Release of some endogenous trace amines from rat striatal slices in the presence and absence of a monoamine oxidase inhibitor. *Life Sci.* 44, 1149-1156;

13 Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;

14 Lindemann, L. et al. (2005) Trace amine associated receptors form structurally and functionally distinct subfamilies of novel G protein-coupled receptors. *Genomics* 85, 372-385.

The invention also provides novel compounds of formula I

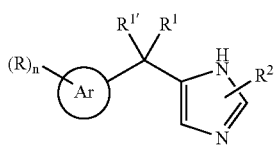

R is hydrogen,
 halogen,
 lower alkyl,
 lower alkoxy,
 hydroxy,
 phenyl,
 S-phenyl or O-phenyl, each of which is optionally substituted by lower alkoxy or halogen,
 benzyloxy,
 C(O)O-lower alkyl,
 cycloalkyl,
 lower alkyl substituted by halogen, or
 lower alkoxy substituted by halogen;
Ar is aryl or heteroaryl, selected from the group consisting of phenyl, naphthyl, pyridinyl, benzofuranyl, dihydrobenzofuranyl and pyrazolyl;
$R^1$ and $R^{1'}$ are each independently hydrogen,
 hydroxy,
 lower alkyl,
 lower alkoxy, or
 phenyl or benzyl, each of which is optionally substituted by halogen;
$R^2$ is hydrogen or lower alkyl; and
n is 1, 2, 3 or 4;
and their pharmaceutically active salts, racemic mixtures, enantiomers, optical isomers and tautomeric forms thereof, with the exception of the following compounds
(S)-4-[1-(2,3-dimethylphenyl)ethyl]-1H-imidazole; Dexmedetomidine
4-(2,3-dimethyl-benzyl)-1H-imidazole; Detomidine
4-(2,6-diethyl-benzyl)-1H-imidazole
4-(2-bromo-benzyl)-1H-imidazole
4-(2-chloro-benzyl)-1H-imidazole
4-(2,6-dimethyl-benzyl)-1H-imidazole
4-benzyl-1H-imidazole
4-(2,3,5,6-tetramethyl-benzyl)-1H-imidazole
4-(3-methoxy-benzyl)-1H-imidazole
4-(2,6-dichloro-benzyl)-1H-imidazole
rac-4-[1-(2,3-dimethyl-phenyl)-ethyl]-2-methyl-1H-imidazole
4-[4-[(4-methoxyphenyl)-sulfanyl]-benzyl]-1H-imidazole
rac-4-[1-(2-methyl-phenyl)-ethyl]-1H-imidazole
rac-4-[1-(2,3-dimethyl-phenyl)-pentyl]-1H-imidazole
4-benzyl-2-methyl-1H-imidazole
4-naphthalen-2-ylmethyl-1H-imidazole
rac-4-(1-naphthalen-1-yl-ethyl)-1H-imidazole
5-(1-methyl-1-phenyl-ethyl)-1H-imidazole trifluoro-acetate
(3H-Imidazol-4-yl)-phenyl-methanol and
4-(1-Naphthalen-1-yl-propyl)-1H-imidazole.

The invention further provides a pharmaceutical composition which comprises a therapeutically effective amount of a compound of the invention and a pharmaceutically acceptable carrier.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain hydrocarbon group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a group having an alkyl residue as defined above which is attached via an oxygen atom.

As used herein, the term "lower alkyl substituted by halogen" denotes an alkyl group as defined above, wherein at least one hydrogen atom is replaced by halogen, for example $CF_3$, $CHF_2$, $CH_2F$, $CH_2CF_3$, $CH_2CF_2CF_3$ and the like.

As used herein, the term "lower alkoxy substituted by halogen" denotes an alkoxy group as defined above, wherein at least one hydrogen atom is replaced by halogen, for example $CF_3$, $CHF_2$, $CH_2F$, $CH_2CF_3$, $CH_2CF_2CF_3$ and the like.

The term "halogen" denotes chlorine, iodine, fluorine and bromine.

The term "cycloalkyl" denotes a saturated cyclic hydrocarbon ring having 3 to 8 carbon atoms as ring members and includes but is not limited to cyclopropyl, cyclobutyl, cyclopentyl, cyclohexyl, cycloheptyl, as well as those groups specifically illustrated by the examples herein below.

The term "alkenyl" denotes a straight- or branched-hydrocarbon chain group containing from 2 to 7 carbon atoms and containing 1, 2 or 3 double bond(s), preferably 1 to 4 carbon atoms and 1 double bond. Examples of such groups are methenyl, 1-ethenyl, 2-ethenyl, 1-propenyl, 2-propenyl, 3-propenyl, isopropenyl, isobutenyl, sec-butenyl, tert-butenyl, pentenyl, and n-hexenyl as well as those specifically illustrated by the examples herein below.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

The present invention provides a method for treating a disorder selected from the group consisting of depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders which comprises administering to an individual a therapeutically effective amount of a compound of formula I

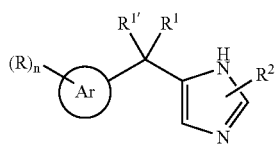

wherein
R is hydrogen,
  halogen,
  lower alkyl,
  lower alkoxy,
  hydroxy,
  phenyl,
  S-phenyl or O-phenyl, each of which is optionally substituted by lower alkoxy or halogen,
  benzyloxy,
  C(O)O-lower alkyl,
  cycloalkyl,
  lower alkyl substituted by halogen, or
  lower alkoxy substituted by halogen;
Ar is aryl or heteroaryl, selected from the group consisting of phenyl, naphthyl, pyridinyl, benzofuranyl, dihydrobenzofuranyl and pyrazolyl;
$R^1$ and $R^{1'}$ are each independently hydrogen,
  hydroxy,
  lower alkyl,
  lower alkoxy, or
  phenyl or benzyl, each of which is optionally substituted by halogen;
$R^2$ is hydrogen or lower alkyl; and
n is 1, 2, 3 or 4;
and their pharmaceutically active salts, racemic mixtures, enantiomers, optical isomers and tautomeric forms.

In the method of the invention, preferred compounds of formula I are those, wherein Ar is phenyl, at least one of $R^1$ and $R^{1'}$ is lower alkyl and $R^2$ is hydrogen, for example the following compounds
rac-4-(1-phenyl-butyl)-1H-imidazole
rac-4-[1-(2-fluoro-phenyl)-ethyl]-1H-imidazole
rac-4-[1-(3,5-difluoro-phenyl)-propyl]-1H-imidazole
rac-4-(1-phenyl-propyl)-1H-imidazole
rac-4-[1-(2-fluoro-phenyl)-propyl]-1H-imidazole
rac-4-[1-(3-fluoro-phenyl)-propyl]-1H-imidazole
rac-4-(1-phenyl-ethyl)-1H-imidazole
rac-4-[1-(3-fluoro-phenyl)-ethyl]-1H-imidazole
rac-4-[1-(2,3-difluoro-phenyl)-ethyl]-1H-imidazole
rac-4-[1-(2,3-difluoro-phenyl)-propyl]-1H-imidazole
5-(1-methyl-1-phenyl-ethyl)-1H-imidazole trifluoro-acetate and
4-[(R)-1-(2,3-Difluoro-phenyl)-ethyl]-1H-imidazole.

Further preferred compounds of formula I for the above method are those, wherein Ar is phenyl, and $R^1$, $R^{1'}$, and $R^2$ are hydrogen, for example the following compounds
4-(4-methoxy-2,3-dimethyl-benzyl)-1H-imidazole
4-(2-chloro-6-fluoro-benzyl)-1H-imidazole
4-(2,3-dimethyl-benzyl)-1H-imidazole; Detomidine
4-(2,6-diethyl-benzyl)-1H-imidazole
4-(2-bromo-benzyl)-1H-imidazole
4-(2,6-dimethyl-benzyl)-1H-imidazole
4-benzyl-1H-imidazole
4-(2,3,5,6-tetramethyl-benzyl)-1H-imidazole
4-(2,6-dichloro-benzyl)-1H-imidazole.
4-(2-ethyl-6-methyl-benzyl)-1H-imidazole
4-(2-cyclopropyl-6-ethyl-benzyl)-1H-imidazole
4-[3-(4-chloro-phenoxy)-benzyl]-1H-imidazole
4-(2-chloro-6-ethyl-benzyl)-1H-imidazole
4-biphenyl-2-ylmethyl-1H-imidazole
4-(2,6-diethyl-4-methoxy-benzyl)-1H-imidazole
4-(2,6-diethyl-3-methoxy-benzyl)-1H-imidazole
4-biphenyl-3-ylmethyl-1H-imidazole
4-(4-ethoxy-2,6-diethyl-benzyl)-1H-imidazole
4-(4-benzyloxy-2,6-diethyl-benzyl)-1H-imidazole
4-(3-ethoxy-2,6-diethyl-benzyl)-1H-imidazole
4-(2-ethyl-6-fluoro-benzyl)-1H-imidazole
4-(2,6-diethyl-4-phenoxy-benzyl)-1H-imidazole and
4-(2,6-diethyl-3-phenoxy-benzyl)-1H-imidazole.

Further preferred compounds for the above mentioned method are those, wherein Ar is naphthyl, for example the following compounds
4-naphthalen-2-ylmethyl-1H-imidazole and
rac-4-(1-naphthalen-1-yl-ethyl)-1H-imidazole.

Further preferred compounds of formula I for the above method are those, wherein Ar is benzofuran-7-yl, for example the following compounds
4-(5-bromo-benzofuran-7-ylmethyl)-1-imidazole and
4-benzofuran-7-ylmethyl-1-imidazole.

Further preferred compounds of formula I for the above mentioned method are those, wherein Ar is dihydrobenzofuran-7yl, for example the compound
4-(2,3-dihydro-benzofuran-7-ylmethyl)-1-imidazole.

Further preferred compounds of formula I for the above mentioned method are those, wherein Ar is pyrazolyl.

Further preferred compounds of formula I for the above mentioned method are those, wherein Ar is pyridinyl.

The invention also provides novel compounds of formula I

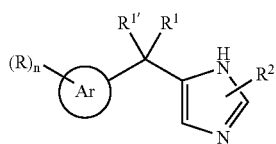

R is hydrogen,
  halogen,
  lower alkyl,
  lower alkoxy,
  hydroxy,
  phenyl,
  S-phenyl or O-phenyl, each of which is optionally substituted by lower alkoxy or halogen,
  benzyloxy,
  C(O)O-lower alkyl,
  cycloalkyl,
  lower alkyl substituted by halogen, or
  lower alkoxy substituted by halogen;
Ar is aryl or heteroaryl, selected from the group consisting of phenyl, naphthyl, pyridinyl, benzofuranyl, dihydrobenzofuranyl and pyrazolyl;
$R^1$ and $R^{1'}$ are each independently hydrogen,
  hydroxy,
  lower alkyl,
  lower alkoxy, or
  phenyl or benzyl, each of which is optionally substituted by halogen;
$R^2$ is hydrogen or lower alkyl; and
n is 1, 2, 3 or 4;
and their pharmaceutically active salts, racemic mixtures, enantiomers, optical isomers and tautomeric forms thereof, with the exception of the following compounds
(S)-4-[1-(2,3-dimethylphenyl)ethyl]-1H-imidazole; Dexmedetomidine
4-(2,3-dimethyl-benzyl)-1H-imidazole; Detomidine
4-(2,6-diethyl-benzyl)-1H-imidazole
4-(2-bromo-benzyl)-1H-imidazole
4-(2-chloro-benzyl)-1H-imidazole
4-(2,6-dimethyl-benzyl)-1H-imidazole
4-benzyl-1H-imidazole
4-(2,3,5,6-tetramethyl-benzyl)-1H-imidazole
4-(3-methoxy-benzyl)-1H-imidazole
4-(2,6-dichloro-benzyl)-1H-imidazole
rac-4-[1-(2,3-dimethyl-phenyl)-ethyl]-2-methyl-1H-imidazole
4-[4-[(4-methoxyphenyl)-sulfanyl]-benzyl]-1H-imidazole
rac-4-[1-(2-methyl-phenyl)-ethyl]-1H-imidazole
rac-4-[1-(2,3-dimethyl-phenyl)-pentyl]-1H-imidazole
4-benzyl-2-methyl-1H-imidazole
4-naphthalen-2-ylmethyl-1H-imidazole
rac-4-(1-naphthalen-1-yl-ethyl)-1H-imidazole
5-(1-methyl-1-phenyl-ethyl)-1H-imidazole trifluoro-acetate
(3H-Imidazol-4-yl)-phenyl-methanol and
4-(1-Naphthalen-1-yl-propyl)-1H-imidazole.
Preferred novel compounds of formula I are those, wherein Ar is phenyl, at least one of $R^1$ or $R^{1'}$ is lower alkyl and $R^2$ is hydrogen, for example the following compounds
rac-4-(1-phenyl-butyl)-1H-imidazole
rac-4-[1-(2-fluoro-phenyl)-ethyl]-1H-imidazole
rac-4-[1-(3,5-difluoro-phenyl)-propyl]-1H-imidazole
rac-4-(1-phenyl-propyl)-1H-imidazole
rac-4-[1-(2-fluoro-phenyl)-propyl]-1H-imidazole
rac-4-[1-(3-fluoro-phenyl)-propyl]-1H-imidazole
rac-4-(1-phenyl-ethyl)-1H-imidazole
rac-4-[1-(3-fluoro-phenyl)-ethyl]-1H-imidazole
rac-4-[1-(2,3-difluoro-phenyl)-ethyl]-1H-imidazole
rac-4-[1-(2,3-difluoro-phenyl)-propyl]-1H-imidazole and
4-[(R)-1-(2,3-difluoro-phenyl)-ethyl]-1H-imidazole.
Further preferred novel compounds of formula I are those, wherein Ar is phenyl, $R^1$, $R^{1'}$, and $R^2$ are hydrogen, for example the following compounds
4-(4-methoxy-2,3-dimethyl-benzyl)-1H-imidazole
4-(2-chloro-6-fluoro-benzyl)-1H-imidazole
4-(2-ethyl-6-methyl-benzyl)-1H-imidazole
4-(2-cyclopropyl-6-ethyl-benzyl)-1H-imidazole
4-[3-(4-chloro-phenoxy)-benzyl]-1H-imidazole
4-(2-chloro-6-ethyl-benzyl)-1H-imidazole
4-biphenyl-2-ylmethyl-1H-imidazole
4-(2,6-diethyl-4-methoxy-benzyl)-1H-imidazole
4-(2,6-diethyl-3-methoxy-benzyl)-1H-imidazole
4-biphenyl-3-ylmethyl-1H-imidazole
4-(4-ethoxy-2,6-diethyl-benzyl)-1H-imidazole
4-(4-benzyloxy-2,6-diethyl-benzyl)-1H-imidazole
4-(3-ethoxy-2,6-diethyl-benzyl)-1H-imidazole
4-(2-ethyl-6-fluoro-benzyl)-1H-imidazole
4-(2,6-diethyl-4-phenoxy-benzyl)-1H-imidazole and
4-(2,6-diethyl-3-phenoxy-benzyl)-1H-imidazole.

The present compounds of formula I and their pharmaceutically acceptable salts can be prepared by methods known in the art, for example, by processes described below, which process comprises
a) catalytically hydrogenating a compound of formula

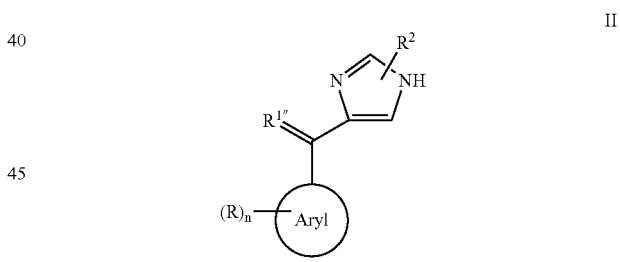

with Pd/C, $H_2$
to obtain a compound of formula

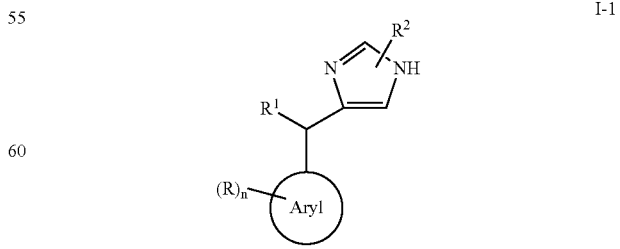

wherein $R^{1''}$ is an alkenyl group, $R^1$ is alkyl and R, $R^2$ and n are as described above, or

9 b) reducing a compound of formula

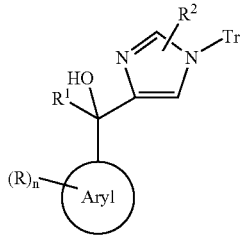

VII with $CF_3CO_2H$ and $Et_3SiH$
to obtain a compound of formula

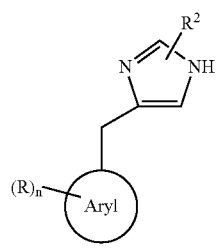

I-2 wherein $R^1$ is hydrogen, and R, $R^2$ and n are as described above, or c) catalytically hydrogenating a compound of formula

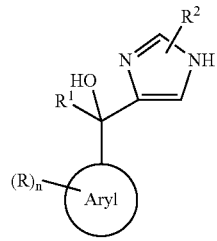

I-3 with Pd/C, $H_2$
to obtain a compound of formula

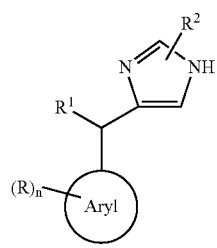

I-1 wherein $R^1$ is lower alkyl, and R, $R^2$ and n are as described above, or

10 d) deprotecting a compound of formula

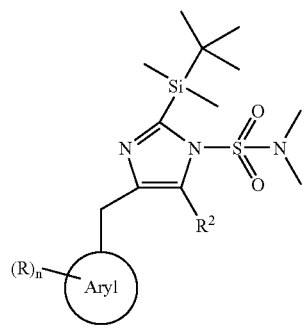

IV with hydrochloric acid
to obtain a compound of formula

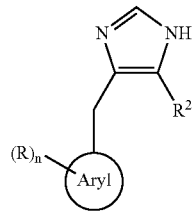

I-5 wherein R, $R^2$ and n are as described above, or e) alkylating a compound of formula

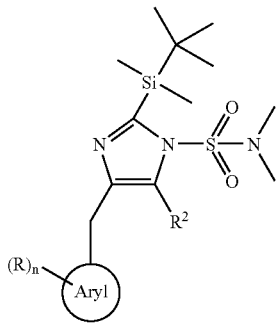

IV with $R^1X$
to obtain a compound of formula

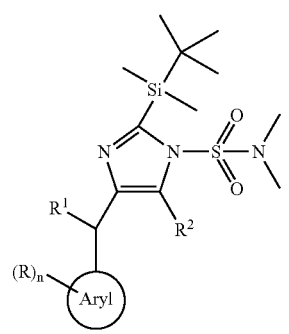

XVII wherein R¹ is lower alkyl, or benzyl optionally substituted by halogen, R, R² and n are as described above and X is halogen, followed by deprotection
with hydrochloric acid
to obtain a compound of formula

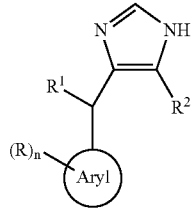
I-4 wherein R, R² and n are as described above, or f) deprotecting a compound of formula

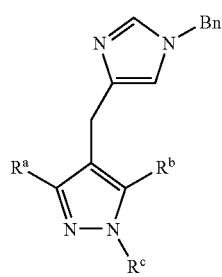
XII with sodium in ammonia or by catalytic hydrogenation with Pd/C, H₂
to obtain a compound of formula

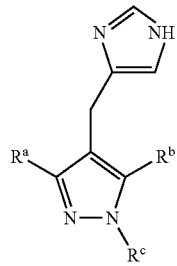
I-6 wherein $R^a$, $R^b$ and $R^c$ are hydrogen, lower alkyl or phenyl, or g) reacting a compound of formula

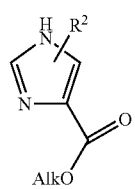
XIV with two equivalents of a Grignard reagent of formula

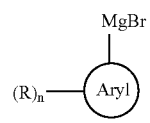
IX to obtain a compound of formula

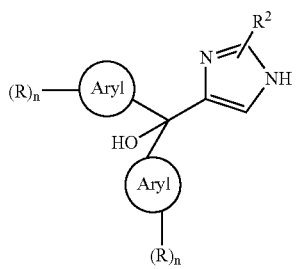
I-7 wherein R is hydrogen, halogen, lower alkyl, lower alkoxy, or phenyl and n is as described above, or h) catalytically hydrogenating a compound of formula

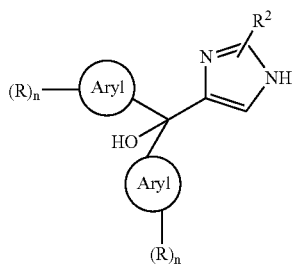
I-7 with Pd/C, H₂
to obtain a compound of formula

I-8 wherein R is hydrogen, lower alkyl, lower alkoxy or phenyl and n is as described above, or i) reducing a compound of formula

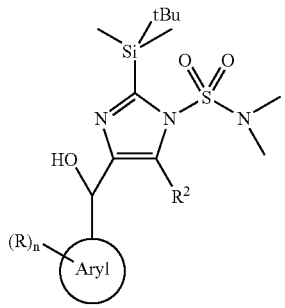

with Pd/C, H$_2$ or with CF$_3$CO$_2$H and Et$_3$SiH
to obtain a compound of formula

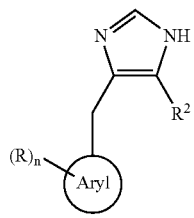

I-5 wherein R$^1$ is hydrogen, and R, R$^2$ and n are as described above, or j) deprotecting a compound of formula

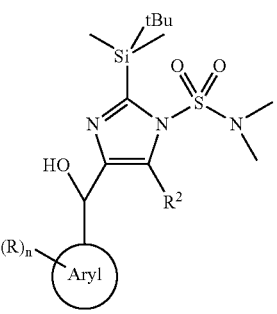

XV with hydrochloric acid in the presence an alcohol of formula AlkOH
to obtain a compound of formula

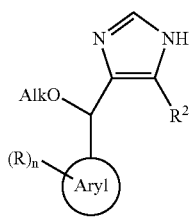

I-5 wherein AlkO is lower alkoxy, and R, R$^2$ and n are as described above, and, if desired, converting the compounds obtained into pharmaceutically acceptable acid addition salts.

The 4-imidazole derivatives of the invention are prepared in analogy to literature procedures following the pathways depicted in Schemes 1 to 6. The starting materials are either commercially available, are otherwise known in the chemical literature, or can be prepared in accordance with methods well known in the art.

PROCEDURE 1

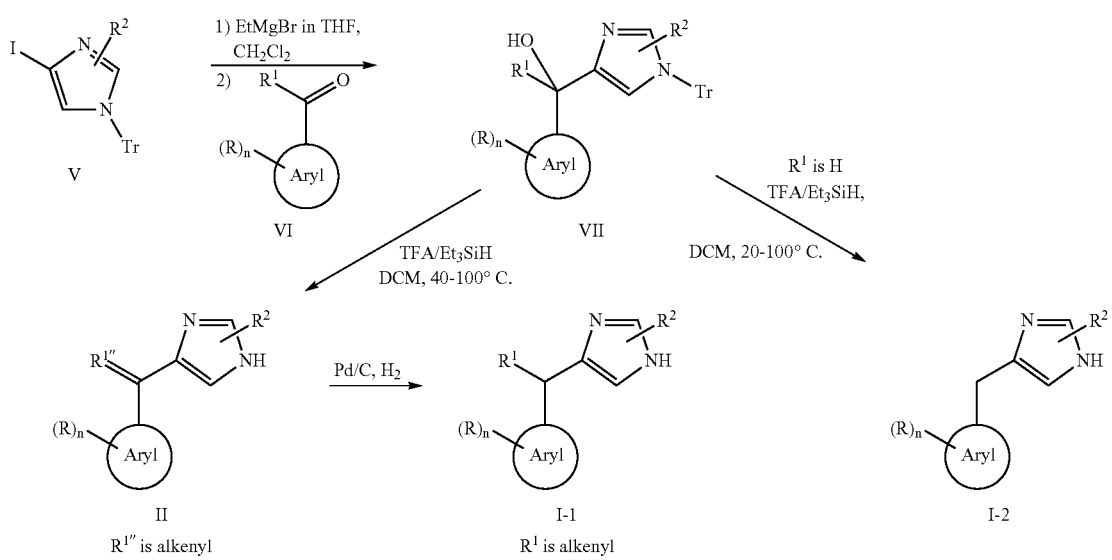

Scheme 1
Preparation of compounds of formula I for R$^1$ being hydrogen or lower alkyl, optionally substituted by halogen, starting from a 4-iodoimidazole Compounds of formula I-1 are obtained by reduction, preferably by a catalytic hydrogenation of the corresponding 4-(1-aryl-alkenyl)-1H-imidazole derivatives II. The catalytic hydrogenation is usually conducted in presence of Pd/C at ambient temperature and normal pressure in an appropriate solvent, preferably ethyl acetate.

The 4-(1-aryl-alkenyl)-1H-imidazoles of formula II are prepared by dehydration and deprotection of corresponding 1-(1H-imidazol-4-yl)-1-aryl-alkanols of formula VII. Treatment of alcohol VII with trifluoroacetic acid (TFA) and triethylsilane in dichloromethane at elevated temperature provides the 4-alkenyl-imidazole. In the case where $R^1$ is hydrogen, it is also possible to obtain compounds of formula I-2 directly from compounds of formula VII, by treatment of alcohol VII with trifluoroacetic acid (TFA) and triethylsilane in dichloromethane at elevated temperature. The reaction can be carried out in a pressure tube in order that the reaction can be operated at temperatures between 20° C. and 100° C.

1-(1H-Imidazol-4-yl)-1-aryl-alkanols of formula VII are synthesized by reaction of the corresponding aryl ketones or aryl aldehydes of formula VI with 4-magnesio-N-trityl-midazole which is generated in situ from 4-iodo-N-trityl-imidazole V and an alkyl Grignard reagent, preferably ethyl magnesium bromide, in an organic solvent, preferably dichloromethane, at ambient temperature for 12 to 36 hours, preferably 16 to 20 hours, following methodology reported in J. Org. Chem. 1991, 56, 5739-5740. The aryl ketones or aryl aldehydes of formula VI are commercially available, are otherwise known in the literature, or can be prepared by methods well known in the art.

PROCEDURE 2

Scheme 2
Preparation of comounds of formula I for $R^1$ being lower alkyl, starting from a 4-acyl-imidazole

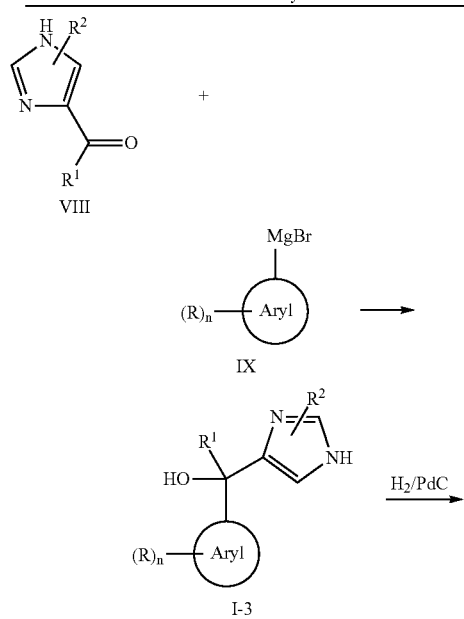

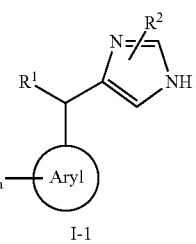

$R^1$ is lower alkyl

Compounds of formula I-1 are obtained by catalytic hydrogenation of 1-(1H-imidazol-4-yl)-1-aryl-alkanols of formula I-3. The catalytic hydrogenation is usually conducted in presence of Pd/C under pressure, usually 5 bar, in an appropriate organic solvent, preferably a lower alcohol or ethyl acetate or a mixture thereof, mixed with an acid, usually hydrochloric acid, at 20° C. to 100° C., preferred 50° C.

1-(1H-Imidazol-4-yl)-1-aryl-alkanols of formula I-3 are prepared from a 4-acyl-imidazole VIII and an aryl Grignard reagent IX following literature known procedures.

PROCEDURE 3

Scheme 3
Preparation of compounds of formula I-4 and I-5 for $R^1/R^{1'}$ being hydrogen, lower alkyl phenyl or benzyl optionally substituted by halogen, starting from I-(N,N-dimethyl-sulfamoyl)-imidazole

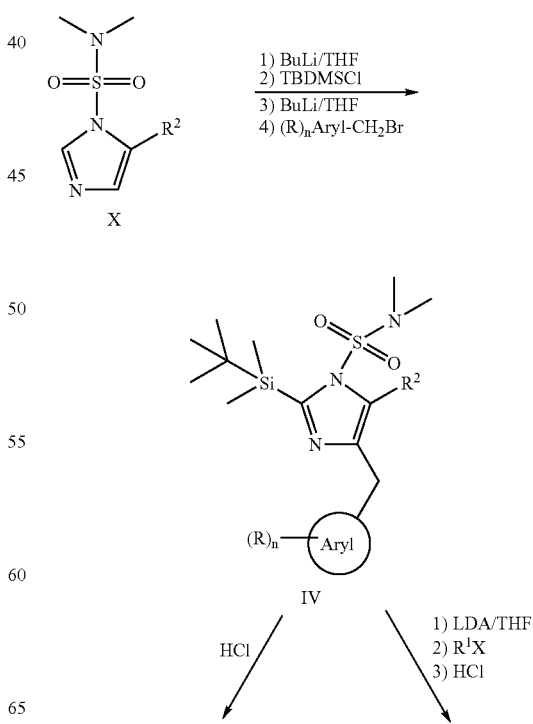

-continued

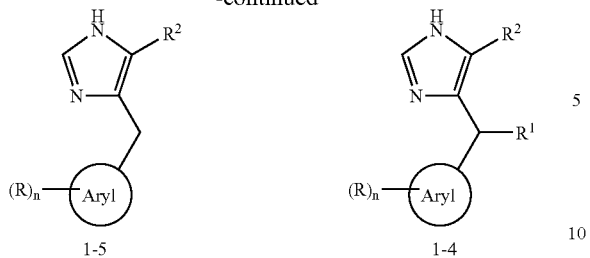

1-5    1-4

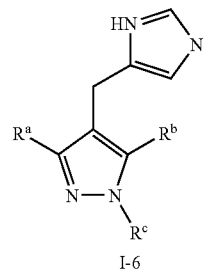

I-6

Compounds of formula I-5 and I-4 can be obtained by deprotection of 4-arylmethyl-2-tert-butyl-dimethylsilanyl-imidazole-1-sulfonic acid dimethylamides of formula IV by heating in diluted strong acid, preferred is 1M to 5M aqueous hydrochloric acid, to reflux temperature for a few hours.

4-Arylmethyl-2-tert-butyl-dimethylsilanyl-imidazole-1-sulfonic acid dimethylamides of formula IV with $R^1/R^{1'}$=H can be deprotonated with a strong base, preferred is lithium diisopropyl amide, in an organic solvent, preferably tetrahydrofuran, and alkylated with halides $R^1X$ wherein $R^1$ is lower alkyl or benzyl, each of which is optionally substituted by halogen, and X being Cl, Br or I.

4-Arylmethyl-2-tert-butyl-dimethylsilanyl-imidazole-1-sulfonic acid dimethylamides of formula IV are synthesized by reaction of an appropriately substituted arylmethyl halide, preferably a bromide, with 4-lithio-2-tert-butyl-dimethylsilanyl-imidazole-1-sulfonic acid dimethylamide which is prepared from 1-(N,N-dimethyl-sulfamoyl)-imidazole X in two steps: a) deprotonation with n-butyl lithium in tetrahydrofuran followed by addition of tert-butyldimethylsilyl chloride which furnishes 2-tert-butyl-dimethylsilanyl-imidazole-1-sulfonic acid dimethylamide; b) n-butyl lithium in tetrahydrofuran which provides 4-lithio-2-tert-butyl-dimethylsilanyl-imidazole-1-sulfonic acid dimethylamide.

PG: Benzyl or other groups compatible with the synthesis
$R^a$, $R^b$ and $R^c$ are hydrogen, alkyl or phenyl.

Pyrazole derivatives of formula XII can be prepared by condensation of a hydrazine derivative of formula XIII with a β-dicarbonyl compound of formula XI bearing at the α-carbon a 1-benzyl-1H-imidazol-4(or -5)-ylmethyl residue. The β-dicarbonyl compounds can be prepared following procedures known in the art.

Debenzylation of the pyrazole derivative of formula XII can be performed either by catalytic hydrogenation or with sodium in liquid ammonia to afford the deprotected compounds of formula I-6. The catalytic hydrogenation is usually conducted in presence of Pd/C under normal conditions or pressure, usually 3 to 100 bar, in an appropriate organic solvent, preferably a lower alcohol or ethyl acetate or a mixture thereof, mixed with an acid, usually hydrochloric acid, at 20° C. to 120° C., preferred 50° C. to 100° C.

PROCEDURE 4

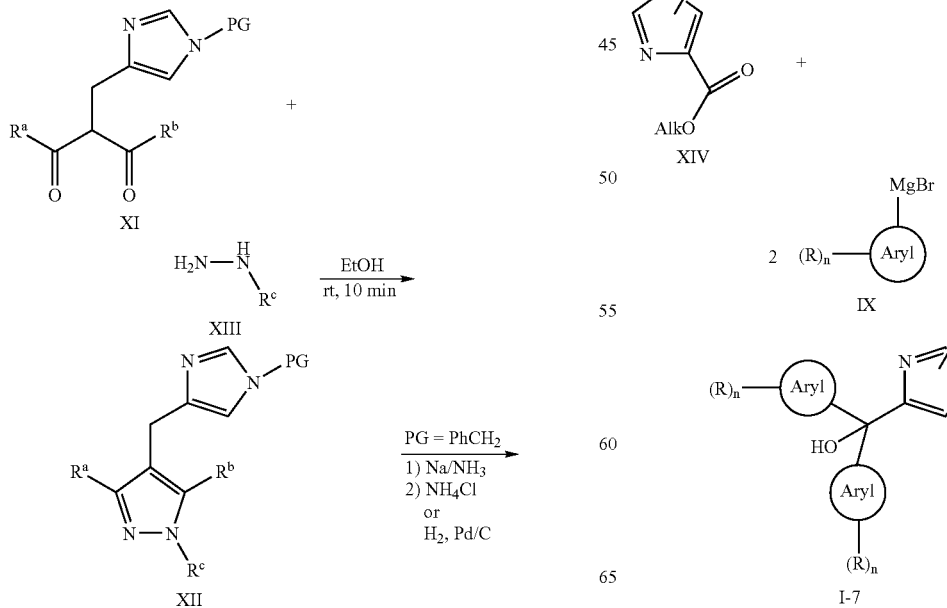

Scheme 4 Preparation of pyrazole derivatives of formula I-6

PROCEDURE 5

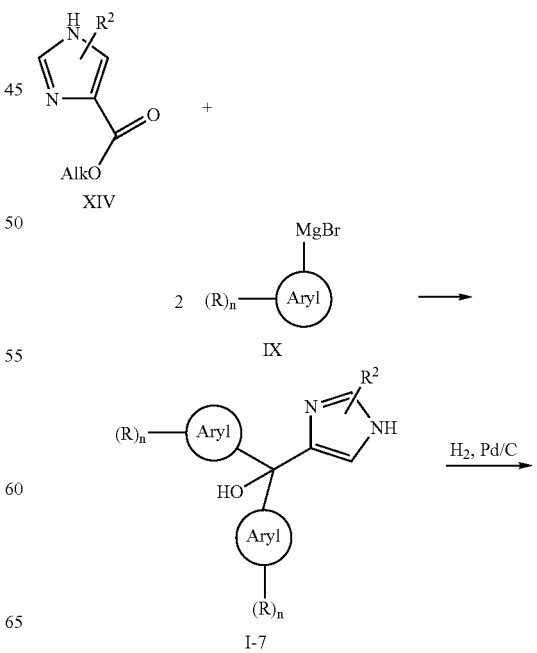

Scheme 5
Preparation of compounds of formula I for $R^1$ being hydrogen or hydroxy and $R^{1'}$ being phenyl, optionally substituted by halogen, starting from an imidazole-4-carboxylic ester -continued

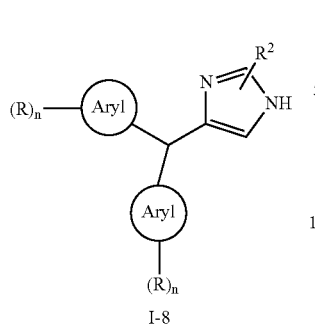

I-8

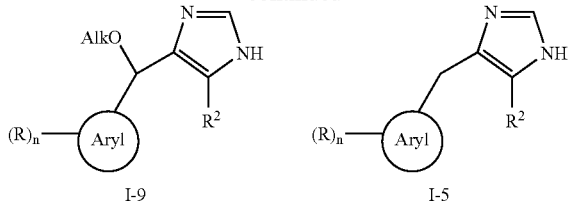

I-9   I-5

Compounds of formula I-8 can be obtained by catalytic hydrogenation of 1-(1H-imidazol-4-yl)-1-aryl-alkanols of formula I-7. The catalytic hydrogenation is usually conducted in presence of Pd/C under pressure, usually 100 bar, in an appropriate organic solvent, preferably a lower alcohol or ethyl acetate or a mixture thereof, mixed with an acid, usually hydrochloric acid, at 20° C. to 120° C., preferred 100° C.

1-(1H-Imidazol-4-yl)-1-aryl-alkanols of formula I-7 can be prepared from an imidazole-4-carboxylic ester XIV and an aryl Grignard reagent IX following procedures known in the literature.

PROCEDURE 6

Scheme 6
Preparation of compounds of formula I-5 for R$^1$ being hydrogen or I-9 for R$^1$ being alkoxy, starting from a protected imidazole compound

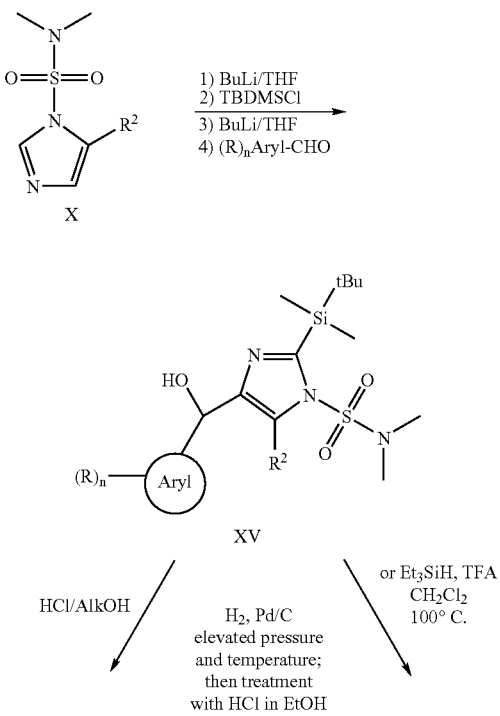

4-Arylmethyl-2-tert-butyl-dimethylsilanyl-imidazole-1-sulfonic acid dimethylamides of formula XV can be synthesized by reaction of an appropriately substituted aryl aldehyde with 4-lithio-2-tert-butyl-dimethylsilanyl-imidazole-1-sulfonic acid dimethylamide which can be prepared in situ from 1-(N,N-dimethyl-sulfamoyl)-imidazole derivative X in two steps: a) deprotonation with n-butyl lithium in tetrahydrofuran followed by addition of tert-butyldimethylsilyl chloride which furnishes 2-tert-butyl-dimethylsilanyl-imidazole-1-sulfonic acid dimethylamide; b) n-butyl lithium in tetrahydrofuran which provides 4-lithio-2-tert-butyl-dimethylsilanyl-imidazole-1-sulfonic acid dimethylamide.

The required aryl aldehydes are either commercially available, are otherwise known in the literature, or can be prepared by methods well known in the art.

Compounds of formula I-9 are obtained by deprotection of XV by heating in alcohol/hydrochloric acid mixtures for a few hours.

Compounds of formula I-5 can be obtained by catalytic hydrogenation of 1-(1H-imidazol-4-yl)-1-aryl-alkanols of formula XV. The catalytic hydrogenation is usually conducted in presence of Pd/C under pressure, usually 100 bar, in an appropriate organic solvent, preferably a lower alcohol or ethyl acetate or a mixture thereof at 20° C. to 100° C., preferred 100° C. Subsequently, deprotection is effected by treatment with HCl in EtOH at 20° C. to 100° C., preferentially 100° C. Alternatively, it is also possible to obtain the compounds of formula I-5 by treatment of the alcohols XV with trifluoroacetic acid (TFA) and triethylsilane in dichloromethane at elevated temperature. The reaction can be carried out in a pressure tube in order that the reaction can be operated at temperatures between 50° C. and 100° C., preferably at 100° C.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and can be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, compounds of the present invention have good affinity to the trace amine associated receptors (TAARs), especially TAAR1.

The compounds were investigated in accordance with the test given hereinafter.

Materials and Methods
Construction of TAAR Expression Plasmids and Stably Transfected Cell Lines For the construction of expression plasmids the coding sequences of human, rat and mouse TAAR 1 were amplified from genomic DNA essentially as described by Lindemann et al. [14]. The Expand High Fidelity PCR System (Roche Diagnostics) was used with 1.5 mM $Mg^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC #CRL-1573) were cultured essentially as described Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable $EC_{50}$ for a culture period of 15 passages were used for all subsequent studies.

Membrane Preparation and Radioligand Binding

Cells at confluence were rinsed with ice-cold phosphate buffered saline without $Ca^{2+}$ and $Mg^{2+}$ containing 10 mM EDTA and pelleted by centrifugation at 1000 rpm for 5 min at 4° C. The pellet was then washed twice with ice-cold phosphate buffered saline and cell pellet was frozen immediately by immersion in liquid nitrogen and stored until use at −80° C. Cell pellet was then suspended in 20 ml HEPES-NaOH (20 mM), pH 7.4 containing 10 mM EDTA, and homogenized with a Polytron (PT 3000, Kinematica) at 10,000 rpm for 10 s. The homogenate was centrifuged at 48,000×g for 30 min at 4° C. and the pellet resuspended in 20 ml HEPES-NaOH (20 mM), pH 7.4 containing 0.1 mM EDTA (buffer A), and homogenized with a Polytron at 10,000 rpm for 10 s. The homogenate was then centrifuged at 48,000×g for 30 min at 4° C. and the pellet resuspended in 20 ml buffer A, and homogenized with a Polytron at 10,000 rpm for 10 s. Protein concentration was determined by the method of Pierce (Rockford, Ill.). The homogenate was then centrifuged at 48,000×g for 10 min at 4° C., resuspended in HEPES-NaOH (20 mM), pH 7.0 including $MgCl_2$ (10 mM) and $CaCl_2$ g protein per ml and (2 mM) (buffer B) at 200 homogenized with a Polytron at 10,000 rpm for 10 s.

Binding assay was performed at 4° C. in a final volume of 1 ml, and with an incubation time of 30 min. The radioligand [$^3$H]-rac-2-(1,2,3,4-tetrahydro-1-naphthyl)-2-imidazoline was used at a concentration equal to the calculated $K_d$ value of 60 nM to give a bound at around 0.1% of the total added radioligand concentration, and a specific binding which represented approximately 70-80% of the total binding. Non-specific binding was defined as the amount of [$^3$H]-rac-2-(1,2,3,4-tetrahydro-1-naphthyl)-2-imidazoline bound in the presence of the appropriate unlabelled ligand (10 µM). Competing ligands were tested in a wide range of concentrations (10 pM-30 µM). The final dimethylsulphoxide concentration in the assay was 2%, and it did not affect radioligand binding. Each experiment was performed in duplicate. All incubations were terminated by rapid filtration through UniFilter-96 plates (Packard Instrument Company) and glass filter GF/C, pre-soaked for at least 2 h in polyethylenimine 0.3%, and using a Filtermate 96 Cell Harvester (Packard Instrument Company). The tubes and filters were then washed 3 times with 1 ml aliquots of cold buffer B. Filters were not dried and soaked in Ultima gold (45 µl/well, Packard Instrument Company) and bound radioactivity was counted by a TopCount Microplate Scintillation Counter (Packard Instrument Company).

The preferred compounds show on mouseTAAR1 a Ki value in the range of 0.003-0.050 µM. Representative compounds are provided in the table below.

| Example | Ki | Example | Ki | Example | Ki | Example | Ki |
|---|---|---|---|---|---|---|---|
| 1 | 0.049 | 20 | 0.018 | 41 | 0.0461 | 67 | 0.0276 |
| 2 | 0.012 | 25 | 0.043 | 46 | 0.0078 | 69 | 0.0026 |
| 4 | 0.028 | 26 | 0.010 | 49 | 0.0009 | 70 | 0.0038 |
| 5 | 0.036 | 27 | 0.034 | 50 | 0.0202 | 71 | 0.0391 |
| 6 | 0.022 | 29 | 0.004 | 51 | 0.0093 | 72 | 0.0127 |
| 7 | 0.032 | 30 | 0.020 | 572 | 0.0056 | 73 | 0.0117 |
| 12 | 0.019 | 31 | 0.016 | 57 | 0.0108 | 74 | 0.0037 |
| 14 | 0.004 | 33 | 0.003 | 58 | 0.0098 | 78 | 0.0179 |
| 15 | 0.019 | 39 | 0.029 | 60 | 0.0276 | 79 | 0.0056 |
| 17 | 0.011 | 40 | 0.003 | 61 | 0.0115 | 80 | 0.0139 |

The present invention also provides pharmaceutical compositions containing compounds of the invention, for example compounds of formula I and their pharmaceutically suitable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those, which include disorders of the central nervous system, for example the treatment or prevention of depression, psychosis, Parkinson's disease, anxiety and attention deficit hyperactivity disorder (ADHD). Thus, the invention provides a method for the treatment of depression, which comprises administering to an individual a therapeutically effective amount of a compound of the invention and a pharmaceutically acceptable carrier. The invention also provides a method for the treatment of psychosis, which comprises administering to an individual a therapeutically effective amount of a compound of the invention and a pharmaceutically acceptable carrier. The invention further provides a method for the treatment of Parkinson's disease, which comprises administering to an individual a therapeutically effective amount of a compound of the invention and a pharmaceutically acceptable carrier. The invention provides a method for the treatment of anxiety, which comprises administering to an individual a therapeutically effective amount of a compound of the invention and a pharmaceutically acceptable carrier. The invention also provides a method for the treatment of attention deficit hyperactivity disorder (ADHD), which comprises administering to an individual a therapeutically effective amount of a compound of the invention and a pharmaceutically acceptable carrier.

The compounds and compositions of the present invention can be administered in a conventional manner, for example, orally, rectally, or parenterally. The compounds of the invention can be administered orally, for example, in the form of tablets, coated tablets, dragées, hard and soft gelatin capsules, solutions, emulsions, or suspensions. The compounds of the invention can be administered rectally, for example, in the form of suppositories or parenterally, for example, in the form of injectable solutions.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

|  |  | mg/tablet | | | |
| --- | --- | --- | --- | --- | --- |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
|  | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

|  |  | mg/capsule | | | |
| --- | --- | --- | --- | --- | --- |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
|  | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXPERIMENTAL

The following examples illustrate the invention but are not intended to limit its scope.

Example 1 rac-4-(1-Phenyl-butyl)-1H-imidazole a) rac-1-Phenyl-1-(1-trityl-1H-imidazol-4-yl)-butan-1-ol

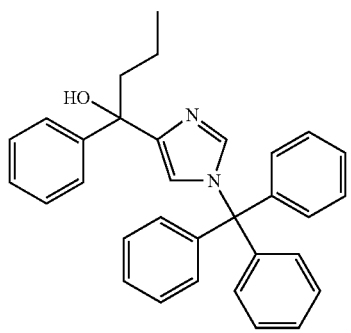

To a solution of 200 mg (0.46 mmol) 4-iodo-1-trityl-imidazole in 3 ml anhydrous dichloromethane was added at ambient temperature 0.16 ml (0.48 mmol) 3M ethyl magnesium bromide in diethyl ether. The mixture was stirred for 1 hour then a solution of 55 mg (0.37 mmol) 1-phenyl-butan-1-one in 0.1 ml anhydrous dichloromethane was added in one portion and the reaction mixture was stirred for 16 hours. Saturated aqueous ammonium chloride (5 ml) was then added to the reaction mixture and the whole was extracted with dichloromethane (3×5 ml). The organic phase was washed with water (3×5 ml) then brine (3×5 ml), dried over MgSO$_4$, concentrated and purified by preparative HPLC to give 90 mg rac-1-phenyl-1-(1-trityl-1H-imidazol-4-yl)-butan-1-ol as colourless oil: MS (ISP): 459.0 ((M+H)$^+$.); $^1$H-NMR (CDCl$_3$): 0.80 (3H, t, CH$_3$), 1.30 (2H, m), 2.05 (2H, m, CH$_2$), 3.45 (1H, s, br, OH), 6.70 (1H, s), 7.05-7.45 (21H, m).

b) (E/Z-)-4-(1-Phenyl-but-1-enyl)-1H-imidazole

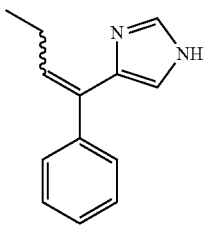

To a solution of 81 mg (0.182 mmol) rac-1-phenyl-1-(1-trityl-1H-imidazol-4-yl)-butan-1-ol in 10 ml trifluoroacetic acid/dichloromethane (1:1) were added 85 mg triethyl silane (115 µl, 0.79 mmol) at ambient temperature. The reaction mixture was heated to reflux for 16 hours and monitored by HPLC. Once all the starting material had been consumed, the reaction mixture was evaporated to dryness. The residue obtained was dissolved in dichloromethane and extracted with 1M HCl (3×10 ml). The aqueous phase was combined, washed with dichloromethane (10 ml) then neutralised to pH 7 with 1M NaOH and extracted with dichloromethane (3×10 ml). The combined organic phase was washed with brine (3×10 ml), dried over MgSO$_4$ and evaporated to give 33 mg (98%) (E/Z-)-4-(1-phenyl-but-1-enyl)-1H-imidazole as colourless oil that did not require further purification. LC @ 215 nm, Rt 1.07 & 1.09 (E and Z isomers): 95%; MS (ISP): 199.0 ((M+H)$^+$.); $^1$H-NMR (CDCl$_3$, E and Z isomers): 0.85-1.10 (2H, t, CH$_3$ and 1H, t, CH$_3$). 2.00-2.30 (1.4H, m, CH$_2$ and 0.6H, m, CH$_2$), 5.95 (1H, t), 7.00 (1H, s), 7.15-7.40 (5H, m), 7.55 (1H, s).

c) rac-4-(1-Phenyl-butyl)-1H-imidazole

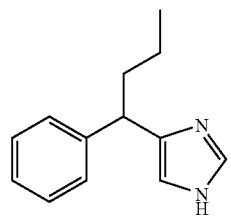

A solution of 33 mg (0.18 mmol) (E/Z-)-4-(1-phenyl-but-1-enyl)-1H-imidazole in 5 ml ethyl acetate was added to 10 mg 10% Pd/C under a nitrogen atmosphere. The nitrogen atmosphere was evacuated and replaced with hydrogen and the reaction mixture was stirred vigorously at ambient temperature and monitored by HPLC until all starting material was consumed. The hydrogen atmosphere was replaced with nitrogen and the reaction mixture was filtered through Celite®. The Celite® was then washed with ethyl acetate (3×5 ml). The filtrate was evaporated and the residue obtained was re-dissolved in 5 ml dichloromethane and extracted with 1M HCl (3×5 ml). The aqueous phase was combined and washed with dichloromethane (5 ml) then was neutralised to pH 7 with 1M NaOH and extracted with dichloromethane (3×5 ml). The combined organic phase was washed with brine (3×5 ml), dried over MgSO$_4$ and evaporated to give the crude alkane as an oil. The alkane was purified by preparative HPLC to give 8 mg, (22%) rac-4-(1-phenyl-butyl)-1H-imidazole as a colourless solid. LC @ 215 nm; Rt 1.21: 100%, MS (ISP): 201.0 ((M+H)$^+$.); $^1$H-NMR (CDCl$_3$): 0.90 (3H, t, CH$_3$), 1.10 (2H, m, CH$_2$), 2.00 (2H, m, CH$_2$), 3.97 (1H, t), 6.89 (1H, s), 7.15-7.35 (5H, m), 7.97 (1H, s) 9.45 (1H, s, br, NH).

Example 2 rac-4-[1-(2-Fluoro-phenyl)-ethyl]-1H-imidazole

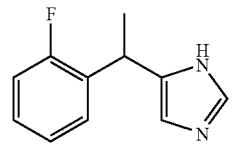

rac-4-[1-(2-Fluoro-phenyl)-ethyl]-1H-imidazole was prepared from 1-(2-fluoro-phenyl)-ethanone following the procedure described for Example 1): colourless powder; MS (ISP): 191.0 ((M+H)$^+$.).

Example 3 rac-4-[1-(3-Trifluoromethyl-phenyl)-propyl]-1H-imidazole

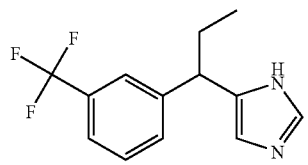

rac-4-[1-(3-Trifluoromethyl-phenyl)-propyl]-1H-imidazole was prepared from 1-(3-trifluoromethyl-phenyl)-propan-1-one following the procedure described for Example 1): colourless powder; MS (ISP): 255.0 ((M+H)$^+$.).

Example 4 rac-4-[1-(3,5-Difluoro-phenyl)-propyl]-1H-imidazole

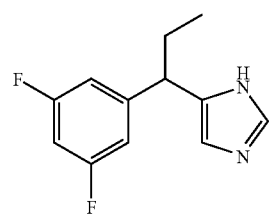

rac-4-[1-(3,5-Difluoro-phenyl)-propyl]-1H-imidazole was prepared from 1-(3,5-difluoro-phenyl)-propan-1-one following the procedure described for Example 1): colourless powder; MS (ISP): 223.0 ((M+H)+.).

Example 5 rac-4-(1-Phenyl-propyl)-1H-imidazole

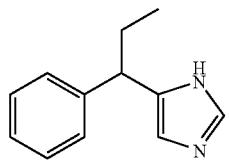

Route A (Procedure 1):

rac-4-(1-Phenyl-propyl)-1H-imidazole was prepared from propiophenone following the procedure described for Example 1): colourless powder; MS (ISP): 187.0 ((M+H)+.).

Route B (Procedure 3):

a) To a solution of 0.30 g (1.71 mmol) 1-(dimethylsulfamoyl)-imidazole in 10 ml tetrahydrofuran were added 1.2 ml (1.88 mmol) of a 1.6M butyl lithium solution in hexane at −75° C. After stirring for 15 min 0.30 g (2 mmol) tert-butyldimethylsilyl chloride was added at −75° C. and the mixture was stirred at ambient temperature for 2 h. The mixture was cooled down again to −75° C. and 1.2 ml (1.88 mmol) of a 1.6M butyl lithium solution in hexane were added. After stirring for 30 min 0.36 g (2.14 mmol) benzylbromide was added at −75° C. and the mixture was allowed to reach room temperature overnight. The mixture was partitioned between water and dichloromethane, re-extracted with dichloromethane and the combined organic layers are dried over MgSO4, filtered and evaporated.

b) For the α-alkylation step an amount of 400 mg (1.05 mmol) of the residue was dissolved in 3 ml tetrahydrofuran and added drop-wise to a freshly prepared solution of lithium diisopropylamide in tetrahydrofuran (from 0.72 ml 1.6M BuLi and 0.128 mg diisopropylamine). After stirring for 1 h at −75° C., 0.197 g (1.26 mmol) ethyl iodide was added, and stirring was continued overnight at ambient temperature. Saturated NH4Cl solution was added to quench the reaction. The aqueous phase was extracted with ethyl acetate (3 times) and the combined organic extracts were dried over MgSO4, filtered and concentrated. The residue was purified by flash chromatography (silica gel, hexanes/ethyl acetate 2:1) to yield 155 mg (36%) 2-(tert-butyl-dimethyl-silanyl)-4-(1-phenyl-propyl)-imidazole-1-sulfonic acid dimethylamide as colourless oil.

c) To remove protecting groups the amount of 155 mg (0.38 mmol) 2-(tert-butyl-dimethyl-silanyl)-4-(1-phenyl-propyl)-imidazole-1-sulfonic acid dimethylamide was dissolved in 10 ml 1.5N hydrochloric acid and refluxed for 1 h. The cooled solution was adjusted to pH>8 with 25% aqueous ammonia and the solution was extracted with dichloromethane (2 times). The combined organic layers are dried over MgSO4, filtered and concentrated. The residue was purified by flash chromatography (silica gel, dichloromethane/methanol/ aqueous conc. ammonia=90:10:1) to yield 71 mg (99%) rac-4-(1-phenyl-propyl)-1H-imidazole as off-white solid: MS (ISP): 187.1 ((M+H)+.).

Example 6 rac-4-[1-(2-Fluoro-phenyl)-propyl]-1H-imidazole

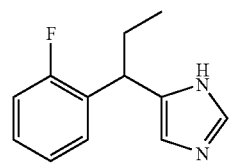

rac-4-[1-(2-Fluoro-phenyl)-propyl]-1H-imidazole was prepared from 1-(2-fluoro-phenyl)-propan-1-one following the procedure described for Example 1): colourless powder; MS (ISP): 205.0 ((M+H)+.).

Example 7 rac-4-[1-(3-Fluoro-phenyl)-propyl]-1H-imidazole

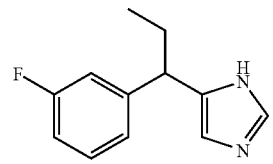

rac-4-[1-(3-Fluoro-phenyl)-propyl]-1H-imidazole was prepared from 1-(3-fluoro-phenyl)-propan-1-one following the procedure described for Example 1): colourless powder; MS (ISP): 205.1 ((M+H)+.).

Example 8 rac-4-(2-Methyl-1-phenyl-propyl)-1H-imidazole

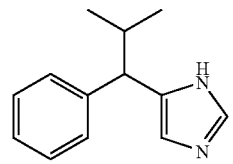

rac-4-(2-Methyl-1-phenyl-propyl)-1H-imidazole was prepared from 2-methyl-1-phenyl-propan-1-one following the procedure described for Example 1): colourless powder; MS (ISP): 201.0 ((M+H)+.).

Example 9 rac-4-Methyl-5-(1-phenyl-ethyl)-1H-imidazole

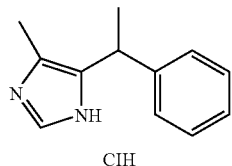

CIH

A 3.0 M solution of phenyl-magnesium bromide (1.3 ml, 4 mmol) in ether was added to a solution of 0.25 g (2.0 mmol) 4-acetyl-5-methyl-imidazole in 20 ml dry tetrahydrofuran at ambient temperature. The mixture was refluxed for 2 h. The solvents are evaporated and the organics are extracted twice with ethyl acetate. The combined organic extracts are concentrated and the residue was purified by flash chromatography (silica gel, dichloromethane/methanol 95:5) to yield a product mainly containing 1-(5-methyl-3H-imidazol-4-yl)-1-phenyl-ethanol. This product was dissolved in 20 ml ethanol/ethyl acetate (1:1) and 0.5 ml of 10M hydrochloric acid was added. The mixture was hydrogenated (5% Pd/C, 0.07 g; 4 bar $H_2$, 50° C.) for 4 h. Then the mixture was filtered through Celite®, and the solvent was evaporated. The residue was partitioned between an aqueous solution of potassium carbonate and ethyl acetate. The organic layer was dried over magnesium sulfate and evaporated to yield a yellow oil that was purified by flash chromatography (silica gel, dichloromethane/methanol 95:5). To the amine an equimolar amount of hydrochloric acid in ethanol (5M) was added. By dilution with ether 4-methyl-5-(1-phenyl-ethyl)-1H-imidazole hydrochloride precipitated as a colourless solid that was filtered off (45 mg, 12%); MS (EI): 186.1 ($M^+$.), 171.1 ((($M-CH_3)^+$.), 100%).

Example 10 rac-4-[1-(2,3-Dimethyl-phenyl)-ethyl]-5-methyl-1H-imidazole hydrochloride or tautomer

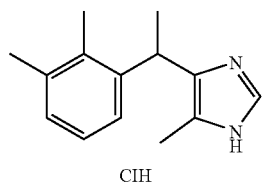

CIH rac-4-[1-(2,3-Dimethyl-phenyl)-ethyl]-5-methyl-1H-imidazole hydrochloride was obtained in comparable yield following the procedure described for Example 9 using 2,3-dimethylphenyl-magnesium bromide instead of phenylmagnesium bromide. MS (EI): 214.1 ($M^+$.), 199.1 ((($M-CH_3)^+$.), 100%).

Example 11

4-(4-Methoxy-2,3-dimethyl-benzyl)-1H-imidazole

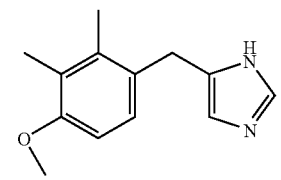

4-(4-Methoxy-2,3-dimethyl-benzyl)-1H-imidazole, MS (ISP): 217.2 ($M+H^+$), was obtained in comparable yield analogous to the procedure described for Example 5 Route B using in step a) 4-methoxy-2,3-dimethylbenzyl chloride instead of benzyl bromide directly followed by deprotection step c).

Example 12

4-(2-Chloro-6-fluoro-benzyl)-1H-imidazole

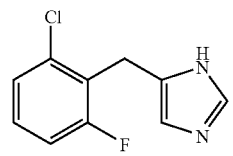

4-(2-Chloro-6-fluoro-benzyl)-1H-imidazole, MS (ISP): 210.3 (($M+H)^+$.), was obtained in comparable yield analogous to the procedure described for Example 5 Route B using in step a) 2-chloro-6-fluorobenzyl bromide instead of benzyl bromide directly followed by deprotection step c).

Example 13

6-tert-Butyl-3-(3H-imidazol-4-ylmethyl)-2,4-dimethyl-phenol hydrochloride

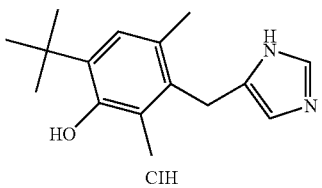

CIH

The title compound, MS (ISP): 259.2 (($M+H)^+$.), was obtained in comparable yield analogous to the procedure described for Example 5 Route B using in step a) 4-tert-butyl-3-hydroxy-2,6-dimethyl-benzyl chloride instead of benzyl bromide directly followed by deprotection step c).

Example 14 rac-4-(1-Phenyl-ethyl)-1H-imidazole

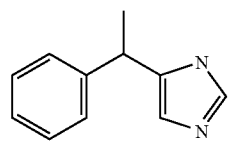

The title compound, MS (EI): 172.1 (M+.), 157.1 (((M-CH₃)+.), 100%) was obtained in comparable yield analogous to the procedure described for Example 5 Route B using in step b) methyl iodide instead of ethyl iodide.

Example 15 rac-4-[1-(3-Fluoro-phenyl)-ethyl]-1H-imidazole

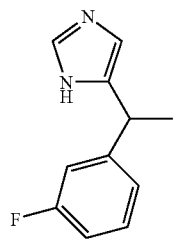

The title compound, MS (ISP): 191.1 (M+H+), was obtained in comparable yield analogous to the procedure described for Example 5 Route B using in step a) 3-fluorobenzyl bromide instead of benzyl bromide and in step b) methyl iodide instead of ethyl iodide.

Example 16 rac-4-[1,2-Bis-(3-fluoro-phenyl)-ethyl]-1H-imidazole

The title compound, MS (ISP): 285.0 (M+H+), was obtained in comparable yield analogous to the procedure described for Example 5 Route B using in step a) 3-fluorobenzyl bromide instead of benzylbromide and in step b) 3-fluorobenzyl bromide instead of ethyl iodide.

Example 17 rac-4-[1-(2,3-Difluoro-phenyl)-ethyl]-1H-imidazole

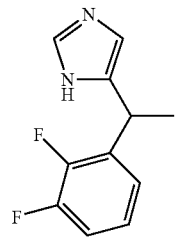

The title compound, MS (EI): 208.1 (M+.) was obtained in comparable yield analogous to the procedure described for Example 5 Route B using in step a) 2,3-difluorobenzyl bromide instead of benzyl bromide and in step b) methyl iodide instead of ethyl iodide.

Example 18

4-(3-Chloro-benzyl)-1H-imidazole

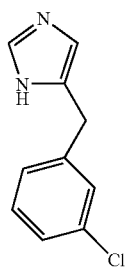

The title compound, MS (ISP): 193.4 (M+H+), was obtained in comparable yield analogous to the procedure described for Example 5 Route B using in step a) 3-chlorobenzyl bromide instead of benzyl bromide directly followed by deprotection step c).

Example 19 rac-4-[1-(2,3-Dimethyl-4-methoxy-phenyl)-ethyl]-1H-imidazole hydrochloride

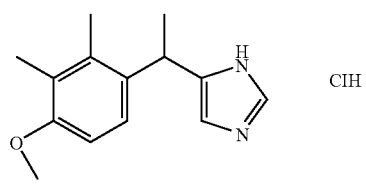

The title compound, MS (ISP): 230.2 (M+H+), was obtained in comparable yield analogous to the procedure described for Example 5 Route B using in step a) 2,3-dimethyl-4-methoxybenzyl chloride instead of benzyl bromide and in step b) methyl iodide instead of ethyl iodide.

Example 20 rac-4-[1-(2,3-Difluoro-phenyl)-propyl]-1H-imidazole

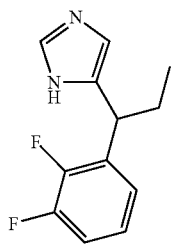

The title compound, MS (EI): 222.1 (M$^+$.), 193.1 (((M-C$_2$H$_5$)$^+$.), 100%) was obtained in comparable yield analogous to the procedure described for Example 5 Route B using in step a) 2,3-difluoro-benzyl chloride instead of benzyl bromide.

Example 21 rac-4-[1-(2,3-Dimethyl-phenyl)-ethyl]-5-butyl-1H-imidazole hydrochloride or tautomer

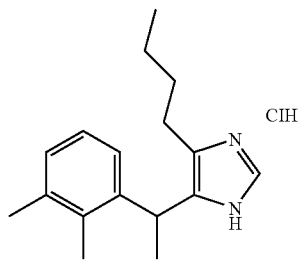

The title compound, MS (ISP): 257.2 (M+H$^+$), was obtained in comparable yield analogous to the procedure described for Example 9 using 2,3-dimethyl-phenylmagnesium bromide instead of phenylmagnesium bromide and 4-acetyl-5-butylimidazole instead of 4-acetyl-5-methylimidazole.

Example 22 rac-4-[1,2-Bis-(3,5-difluoro-phenyl)-ethyl]-1H-imidazole

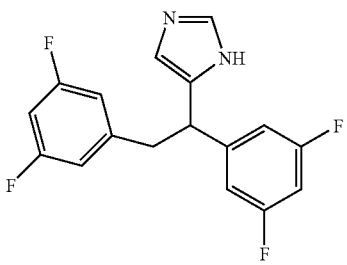

The title compound, MS (ISP): 321.1 (M+H$^+$), was obtained in comparable yield analogous to the procedure described for Example 5 Route B using in step a) 3,5-difluorobenzyl bromide instead of benzyl bromide and in step b) 3,5-difluorobenzyl bromide instead of ethyl iodide.

Example 23 rac-5-[1-(2,3-Difluoro-phenyl)-propyl]-2-methyl-1H-imidazole or tautomer

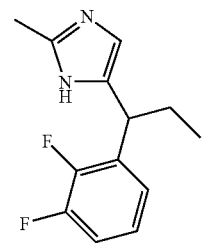

The title compound, MS (EI): 236.1 (M$^+$.), 207.1 (((M-C$_2$H$_5$)$^+$.), 100%) was obtained analogous to the procedure described for Example 5 Route B using 1-(dimethylsulfamoyl)-2-methyl-imidazole instead of 1-(dimethylsulfamoyl)-imidazole and 2,3-difluorobenzyl bromide instead of benzyl bromide in step a).

Known Compounds:

| Example No. | Structure | | Name |
|---|---|---|---|
| 24 | 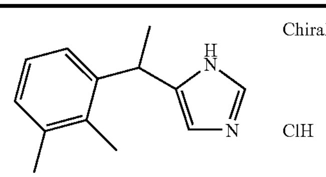 | Chiral<br><br>ClH | (S)-4-[1-(2,3-dimethylphenyl)ethyl]-1H-imidazole;<br>Dexmedetomidine |

-continued
| Example No. | Structure | Name |
|---|---|---|
| 25 | 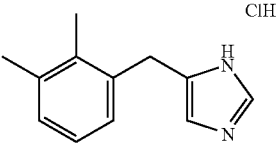 | 4-(2,3-Dimethyl-benzyl)-1H-imidazole; Detomidine |
| 26 | 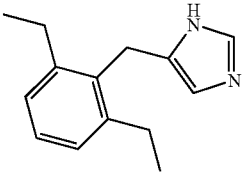 | 4-(2,6-Diethyl-benzyl)-1H-imidazole |
| 27 | 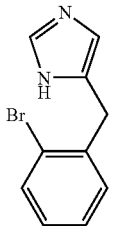 | 4-(2-Bromo-benzyl)-1H-imidazole |
| 28 | 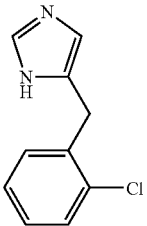 | 4-(2-Chloro-benzyl)-1H-imidazole |
| 29 | 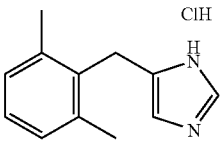 | 4-(2,6-Dimethyl-benzyl)-1H-imidazole |
| 30 | 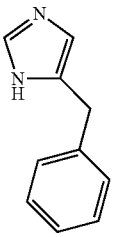 | 4-Benzyl-1H-imidazole |
| 31 | 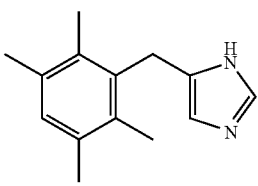 | 4-(2,3,5,6-Tetramethyl-benzyl)-1H-imidazole |

| Example No. | Structure | Name |
|---|---|---|
| 32 | 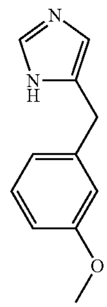 | 4-(3-Methoxy-benzyl)-1H-imidazole |
| 33 | 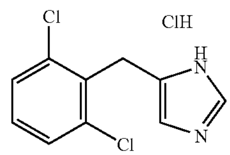 | 4-(2,6-Dichloro-benzyl)-1H-imidazole |
| 34 | 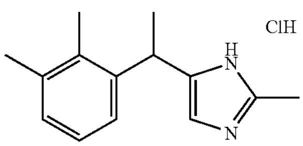 | rac-4-[1-(2,3-Dimethyl-phenyl)-ethyl]-2-methyl-1H-imidazole or tautomer |
| 35 | 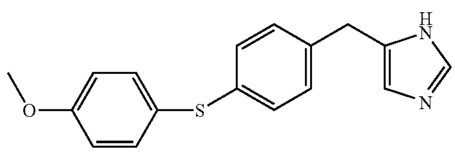 | 4-[4-[(4-methoxyphenyl)-sulfanyl]-benzyl]-1H-imidazole |
| 36 | 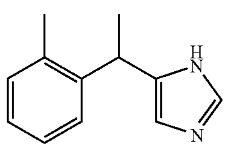 | rac-4-[1-(2-Methyl-phenyl)-ethyl]-1H-imidazole |
| 37 | 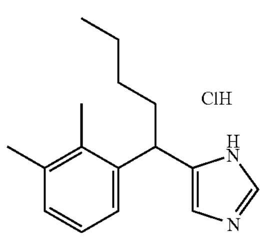 | rac-4-[1-(2,3-Dimethyl-phenyl)-pentyl]-1H-imidazole |
| 38 | 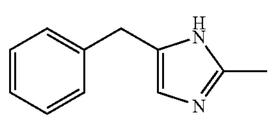 | 4-Benzyl-2-methyl-1H-imidazole or tautomer |
| 39 | 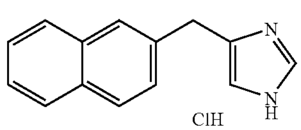 | 4-Naphthalen-2-ylmethyl-1H-imidazole |

-continued

| Example No. | Structure | Name |
|---|---|---|
| 40 | 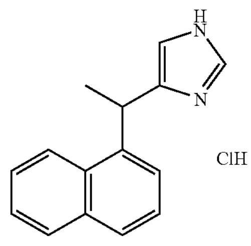 | rac-4-(1-Naphthalen-1-yl-ethyl)-1H-imidazole |
| 41 | 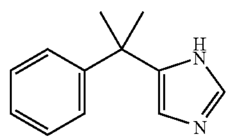 | 5-(1-methyl-1-phenyl-ethyl)-1H-imidazole trifluoro-acetate |
| 42 | 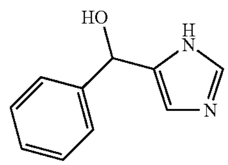 | (3H-Imidazol-4-yl)-phenyl-methanol |
| 43 | 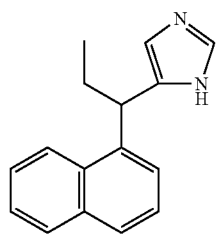 | 4-(1-Naphthalen-1-yl-propyl)-1H-imidazole |

Example 44 rac-5-(Methoxy-phenyl-methyl)-1H-imidazole

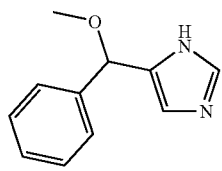

a) 2-(tert-Butyl-dimethyl-silanyl)-4-(hydroxy-phenyl-methyl)-imidazole-1-sulfonic acid dimethylamide

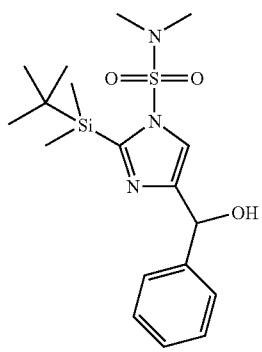

To a solution of 0.30 g (1.71 mmol) 1-(dimethylsulfamoyl)-imidazole in 10 ml tetrahydrofuran were added 1.2 ml (1.88 mmol) of a 1.6M butyl lithium solution in hexane at −75° C. After stirring for 15 min 0.30 g (2 mmol) tert-butyldimethylsilyl chloride was added at −75° C. and the mixture was stirred at ambient temperature for 2 h. The mixture was cooled down again to −75° C. and 1.2 ml (1.88 mmol) of a 1.6M butyl lithium solution in hexane were added. After stirring for 30 min 0.22 ml (2.14 mmol) benzaldehyde was added at −75° C. and the mixture was allowed to reach room temperature overnight. The mixture was partitioned between water and dichloromethane, re-extracted with dichloromethane and the combined organic layers are dried over MgSO$_4$, filtered and evaporated to yield 0.73 g of an yellow oil, that was used directly in the next step, MS (EI): 338.1 ((M-tBu)$^+$.).

b) rac-5-(Methoxy-phenyl-methyl)-1H-imidazole

A gentle stream of HCl gas was bubbled through a refluxing solution of 2-(tert-butyl-dimethyl-silanyl)-4-(hydroxy-phenyl-methyl)-imidazole-1-sulfonic acid dimethylamide (0.2 g, 0.51 mmol) in methanol (5 ml) for 1 hour. The solvent was evaporated and sodium hydroxide solution was added. The mixture was extracted with dichloromethane (2 times). The combined organic layers are dried over MgSO$_4$, filtered and concentrated. The residue was purified by flash chromatography (silica gel, dichloromethane/methanol/aqueous conc. ammonia=90:10:1) to yield 25 mg (26%) of rac-5-

(hydroxy-phenyl-methyl)-1H-imidazole, MS (EI): 174.1 ((M+.) and 5 mg (5%) of rac-5-(methoxy-phenyl-methyl)-1H-imidazole as colourless oil: MS (ISP): 189.1 ((M+H)+.).

Example 45 and 46

4-[(S)-1-(2,3-Difluoro-phenyl)-ethyl]-1H-imidazole and 4-[(R)-1-(2,3-Difluoro-phenyl)-ethyl]-1H-imidazole

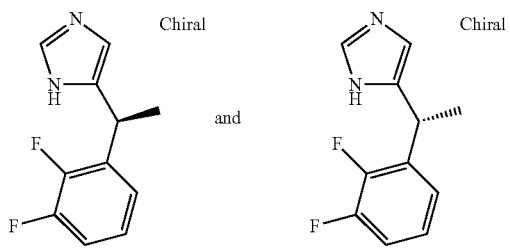

a) 2-(tert-Butyl-dimethyl-silanyl)-4-(2,3-difluoro-benzyl)-imidazole-1-sulfonic acid dimethylamide

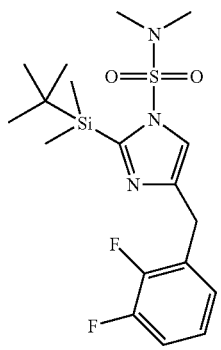

To a solution of 4.2 g (14.5 mmol) 2-(tert-butyl-dimethyl-silanyl)-imidazole-1-sulfonic acid dimethylamide in 50 ml tetrahydrofuran were added 10.9 ml (17.4 mmol) of a 1.6M butyl lithium solution in hexane at −75° C. After stirring for 20 min 3.6 g (17.4 mmol) 2,3-difluorobenzylbromide was added at −75° C. and the mixture was allowed to reach room temperature overnight. The mixture was partitioned between water and ethyl acetate, re-extracted with ethyl acetate and the combined organic layers are dried over MgSO4, filtered and evaporated. The residue was purified by flash chromatography (silica gel, hexane/ethyl acetate=4:1) to yield 3.0 g (49%) of 2-(tert-butyl-dimethyl-silanyl)-4-(2,3-difluoro-benzyl)-imidazole-1-sulfonic acid dimethylamide as a light yellow solid; MS (ISP): 416.1 ((M+H)+.).

b) (−)- and (+)-2-(tert-Butyl-dimethyl-silanyl)-4-[1-(2,3-difluoro-phenyl)-ethyl]-imidazole-1-sulfonic acid dimethylamide

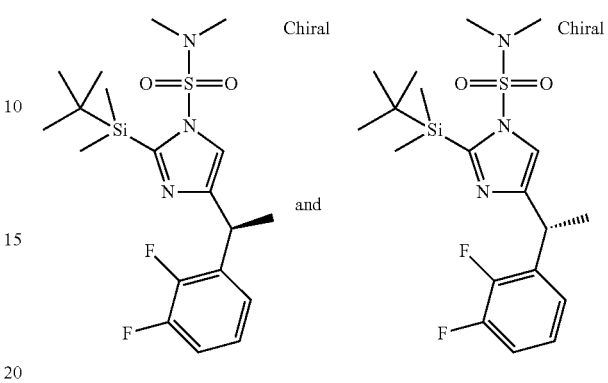

An amount of 2.9 g (7.0 mmol) of 2-(tert-butyl-dimethyl-silanyl)-4-(2,3-difluoro-benzyl)-imidazole-1-sulfonic acid dimethylamide was dissolved in 30 ml tetrahydrofuran and added drop-wise to a freshly prepared solution of lithium diisopropylamide in tetrahydrofuran (from 6.54 ml 1.6M BuLi and 1.06 g diisopropylamine). After stirring for 1 h at −75° C., 1.14 g (8.0 mmol) methyl iodide was added, and stirring was continued overnight at ambient temperature. Water was added to quench the reaction. The aqueous phase was extracted with ethyl acetate (3 times) and the combined organic extracts were dried over MgSO4, filtered and concentrated. The residue was purified by flash chromatography (silica gel, hexanes/ethyl acetate 4:1) to yield 2.47 g of rac-2-(tert-butyl-dimethyl-silanyl)-4-[1-(2,3-difluoro-phenyl)-ethyl]-imidazole-1-sulfonic acid dimethylamide (MS (ISP): 430.3 ((M+H)+.), light yellow oil). This material was separated by chiral column chromatography (Chiral OD, isopropanol/heptane=2:98) to yield 0.785 g (26%) of (+)-2-(tert-butyl-dimethyl-silanyl)-4-[1-(2,3-difluoro-phenyl)-ethyl]-imidazole-1-sulfonic acid dimethylamide and 0.946 g (32%) of (+)-2-(tert-butyl-dimethyl-silanyl)-4-[1-(2,3-difluoro-phenyl)-ethyl]-imidazole-1-sulfonic acid dimethylamide.

c) 4-[(S)-1-(2,3-Difluoro-phenyl)-ethyl]-1H-imidazole and 4-[(R)-1-(2,3-Difluoro-phenyl)-ethyl]-1H-imidazole (+)-2-(tert-Butyl-dimethyl-silanyl)-4-[1-(2,3-difluoro-phenyl)-ethyl]-imidazole-1-sulfonic acid dimethylamide (350 mg, 0.81 mmol) was dissolved in 10 ml 1.5N hydrochloric acid and refluxed for 1 h. The cooled solution was adjusted to pH>8 with 25% aqueous ammonia and the solution was extracted with dichloromethane (2 times). The combined organic layers are dried over MgSO4, filtered and concentrated. The residue was purified by flash chromatography (silica gel, dichloromethane/methanol/aqueous conc. ammonia=90:10:1) to yield 80 mg (47%) of 4-[1-(2,3-difluoro-phenyl)-ethyl]-1H-imidazole (Enantiomer 1) as off-white solid: MS (ISP): 208.9 ((M+H)+.), chiral HPLC (Reprosil Chiral-NR; heptane/ethanol=90:10): $t_R$=9.9 min. 4-[1-(2,3-Difluoro-phenyl)-ethyl]-1H-imidazole (Enantiomer 2) was obtained by the same procedure from (−)-2-(tert-butyl-dimethyl-silanyl)-4-[1-(2,3-difluoro-phenyl)-ethyl]-imidazole-1-sulfonic acid dimethylamide in 73% yield; colourless oil, MS (ISP): 208.9 ((M+H)+.), chiral HPLC (Reprosil Chiral-NR; heptane/ethanol=90:10): $t_R$=11.1 min.

Example 47

Bis-(3,5-difluoro-phenyl)-(1H-imidazol-4-yl)-methanol

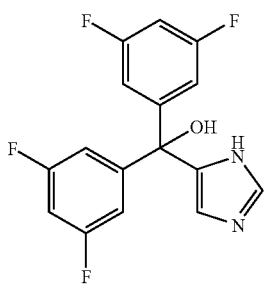

Methyl 4-imidazolecarboxylate 0.80 g (6.34 mmol) was placed in a flask and under argon 50 ml (25 mmol) of a 0.5M 3,5-difluorophenylmagnesium bromide solution in tetrahydrofuran were added. The mixture was refluxed for 2 hours and then most of the solvent was evaporated. Water was added with cooling, and the mixture was extracted twice with ethyl acetate. The combined organic extracts were concentrated and the residue was purified by flash chromatography (silica gel, heptane/ethyl acetate 8:2) to yield 1.5 g (73%) of bis-(3,5-difluoro-phenyl)-(1H-imidazol-4-yl)-methanol as a white solid; MS (ISP): 305.1 ((M-OH)+); 323.4 ((M+H)+.).

Example 48

4-[Bis-(3,5-difluoro-phenyl)-methyl]-1H-imidazole

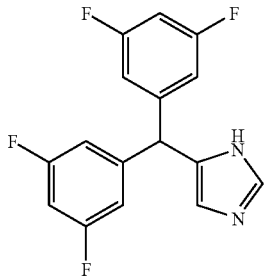

Bis-(3,5-difluoro-phenyl)-(1H-imidazol-4-yl)-methanol (0.5 g, 1.55 mmol) was dissolved in 10 ml ethanol and 0.66 ml of 12M hydrochloric acid was added. The mixture was hydrogenated (5% Pd/C, 0.07 g; 100 bar $H_2$, 100° C.) for 20 h. Then the mixture was filtered through Celite®, and the solvent was evaporated. The residue was partitioned between an aqueous solution of potassium carbonate and ethyl acetate. The organic layer was dried over magnesium sulfate and evaporated. The residue was purified by flash chromatography (silica gel, ethyl acetate) to yield 0.2 g (42%) of 4-[bis-(3,5-difluoro-phenyl)-methyl]-1H-imidazole as a white solid; MS (ISP): 307.1 ((M+H)+.).

Example 49

4-(5-Bromo-benzofuran-7-ylmethyl)-1-imidazole a) 4-(5-Bromo-benzofuran-7-ylmethyl)-2-(tert-butyl-dimethyl-silanyl)-imidazole-1-sulfonic acid dimethylamide

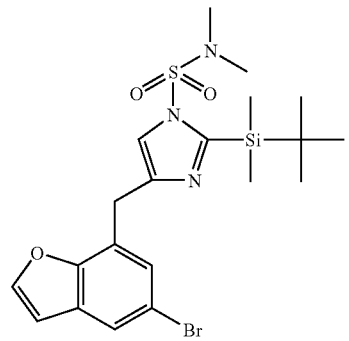

4-(5-Bromo-benzofuran-7-ylmethyl)-2-(tert-butyl-dimethyl-silanyl)-imidazole-1-sulfonic acid dimethylamide was prepared in analogy to Example 5 (Route B, step a), using 5-bromo-7-bromomethyl-benzofuran instead of benzyl bromide: light yellow amorphous solid; MS (ISP): 500.0 ((M+H)+.).

b) 4-(5-Bromo-benzofuran-7-ylmethyl)-1-imidazole

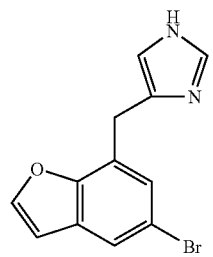

4-(5-Bromo-benzofuran-7-ylmethyl)-1-imidazole was prepared in analogy to Example 5 (Route B, step c) from 4-(5-bromo-benzofuran-7-ylmethyl)-2-(tert-butyl-dimethyl-silanyl)-imidazole-1-sulfonic acid dimethylamide: white solid; MS (ISP): 277.0 ((M+H)+.).

Example 50

4-(2,3-Dihydro-benzofuran-7-ylmethyl)-1-imidazole

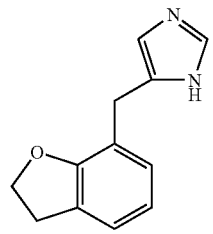

A solution of 4-(5-bromo-benzofuran-7-ylmethyl)-1-imidazole (21 mg; example 49) in EtOH (2 ml) was treated with 10% Pd/C (10 mg) and hydrogenated under normal pressure for 20 hrs. The reaction mixture was filtrated and concentrated. The crude product was purified by column chromatography (Isolute® Flash-NH₂ (Separtis); gradient: CH₂Cl₂→CH₂Cl₂/MeOH 95:5) to give 4-(2,3-dihydro-benzofuran-7-ylmethyl)-1-imidazole (7 mg) as white solid.

Example 51

4-Benzofuran-7-ylmethyl-1-imidazole

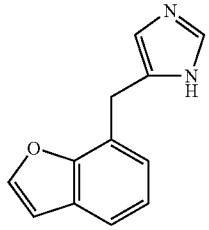

4-Benzofuran-7-ylmethyl-1-imidazole was prepared in analogy to example 49 starting from 7-bromomethyl-benzofuran: light yellow solid; MS (ISP): 199.1 ((M+H)⁺.).

Example 52

4-(2-Methyl-naphthalen-1-ylmethyl)-1H-imidazole

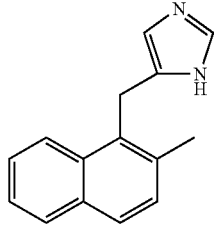

4-(2-Methyl-naphthalen-1-ylmethyl)-1H-imidazole was prepared in analogy to example 49 starting from 1-bromomethyl-2-methyl-naphthalene: white solid; MS (ISP): 223.1 ((M+H)⁺.).

Example 53

Rac-7-[Hydroxy-(1H-imidazol-4-yl)-methyl]-5-methyl-benzofuran-2-carboxylic acid ethyl ester a) 7-Formyl-5-methyl-benzofuran-2-carboxylic acid ethyl ester

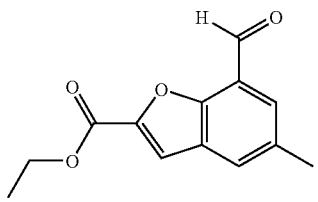

A solution of 2-hydroxy-5-methylisophtalaldehyde (1 g) in DMF (10 ml) was treated under an Argon atmoprhere with potassium carbonate (1.01 g) and diethyl bromomalonate (1.60 g). The reaction mixture was heated to 100° C. for 20 hrs, then cooled to r.t., quenched with water and extracted with EtOAc. The organics were dried over MgSO₄, filtrated and concentrated to obtain 7-formyl-5-methyl-benzofuran-2-carboxylic acid ethyl ester (1.34 g) as off-white solid. MS (ISP): 233.1 ((M+H)⁺.). The crude product was used in the next reaction step without further purification.

b) Rac-7-{[2-(tert-Butyl-dimethyl-silanyl)-1-dimethylsulfamoyl-1H-imidazol-4-yl]-hydroxy-methyl}-5-methyl-benzofuran-2-carboxylic acid ethyl ester

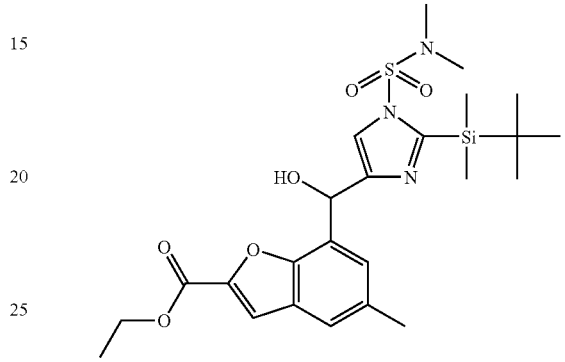

A solution of 2-(tert-butyl-dimethyl-silanyl)-imidazole-1-sulfonic acid dimethylamide (1.0 g) in THF (10 ml) was cooled under an Argon atmosphere to −78° C. n-Buthyl-lithium solution (1.6 M in heptane, 2.37 ml) were added dropwise. After stirring for 1 hr at −78° C. a solution of 7-formyl-5-methyl-benzofuran-2-carboxylic acid ethyl ester (963 mg) in THF (10 ml) was added dropwise. Stirring was continued for 15 min at −78° C., then the reaction mixture was warmed up to r.t. overnight. After quenching with water, the mixture was extracted with EtOAc. The organics were dried over MgSO4, filtrated and concentrated. The crude product was purified by column chromatography (silica gel; gradient: cyclohexane→cyclohexane/EtOAc 1:1) to give rac-7-{[2-(tert-butyl-dimethyl-silanyl)-1-dimethylsulfamoyl-1H-imidazol-4-yl]-hydroxy-methyl}-5-methyl-benzofuran-2-carboxylic acid ethyl ester as light yellow amorphous solid; MS (ISP): 522.3 ((M+H)⁺.).

c) Rac-7-[Hydroxy-(1H-imidazol-4-yl)-methyl]-5-methyl-benzofuran-2-carboxylic acid ethyl ester

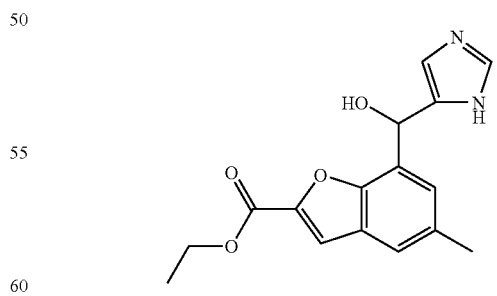

Rac-7-[Hydroxy-(1H-imidazol-4-yl)-methyl]-5-methyl-benzofuran-2-carboxylic acid ethyl ester was prepared in analogy to Example 5 (Route B, step c) from 7-{[2-(tert-butyl-dimethyl-silanyl)-1-dimethylsulfamoyl-1H-imidazol-4-yl]-hydroxy-methyl}-5-methyl-benzofuran-2-carboxylic acid ethyl ester: white solid; MS (ISP): 301.3 ((M+H)⁺.).

Example 54

7-(1H-Imidazol-4-ylmethyl)-5-methyl-benzofuran-2-carboxylic acid ethyl ester

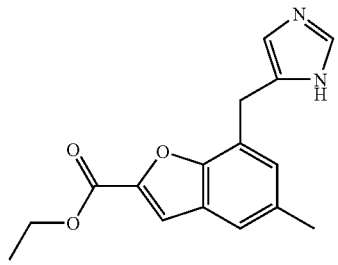

A solution of rac-7-{[2-(tert-butyl-dimethyl-silanyl)-1-dimethylsulfamoyl-1H-imidazol-4-yl]-hydroxy-methyl}-5-methyl-benzofuran-2-carboxylic acid ethyl ester (470 mg; example 52.b) in EtOH (16 ml) was treated with 10% Pd/C (117 mg) and hydrogenated for 48 hrs at 100 bar and 100° C. The reaction mixture was cooled to r.t., filtrated and concentrated. The residue was dissolved in EtOH (5 ml) and treated with 3N HCl (5 ml). The solution was heated to 100° C. for 3 hrs, then concentrated. The residue was taken up in water. The solution was made basic by the addition of $K_2CO_3$ and extracted with $CH_2Cl_2$/MeOH 4:1. The organics were dried over $MgSO_4$, filtrated and concentrated. The crude product was purified by column chromatography (silica gel; gradient: $CH_2Cl_2 \rightarrow CH_2Cl_2$/MeOH 9:1) to give 7-(1H-imidazol-4-ylmethyl)-5-methyl-benzofuran-2-carboxylic acid ethyl ester (10 mg) as amorphous off-white solid. MS (ISP): 285.1 ((M+H)$^+$.).

Example 55

3,5-Diethyl-4-(3H-imidazol-4-ylmethyl)-1H-pyrazole

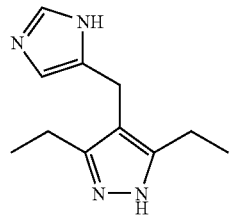

a) 4-(3-Benzyl-3H-imidazol-4-ylmethyl)-heptane-3,5-dione or 4-(1-Benzyl-1H-imidazol-4-ylmethyl)-heptane-3,5-dione

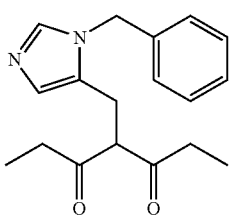

or

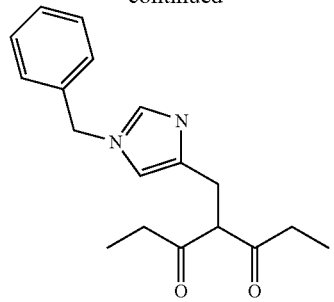

To a solution of 3.75 ml (10 mmol; ~21% solution in ethanol) sodium ethanolate in 40 ml dry ethanol were added 1.30 mg (10 mmol) 3,5-heptanedione and stirred at 50° C. for 30 min. Then a tip of spatula of potassium iodide was added followed by a solution of 1-benzyl-5-chloromethyl-1H-imidazole (prepared from 2.27 g (9.4 mmol) 1-benzyl-5-chloromethyl-1H-imidazole hydrochloride in 10 ml ethanol and 3.5 ml (9.4 mmol; ~21% solution in ethanol). The mixture was heated to 50° C. for further 5 min and then immediately cooled to ambient temperature and concentrated under reduced pressure at max. 30° C. Purification by flash-chromatography on silica gel with heptane/ethyl acetate 1:1 as eluent provided 4-(3-benzyl-3H-imidazol-4-ylmethyl)-heptane-3,5-dione as light yellow waxy solid: MS (ISP): 299.2 ((M+H)$^+$.).

b) 4-(3-Benzyl-3H-imidazol-4-ylmethyl)-3,5-diethyl-1H-pyrazole or 4-(1-Benzyl-1H-imidazol-4-ylmethyl)-3,5-diethyl-1H-pyrazole

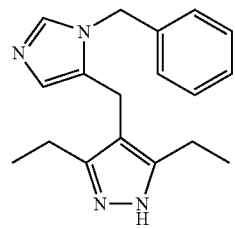

or

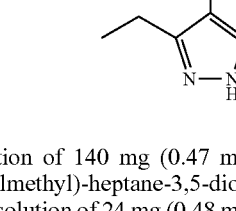

To a solution of 140 mg (0.47 mmol) 4-(3-benzyl-3H-imidazol-4-ylmethyl)-heptane-3,5-dione in 1.5 ml ethanol was added a solution of 24 mg (0.48 mmol) hydrazine monohydrate in 0.5 ml ethanol and the mixture heated to reflux for 10 min. The reaction mixture was evaporated under reduced pressure, the residue dissolved in 1N aqueous HCl solution and extracted three times with t-butyl methyl ether. The aqueous phase was adjusted to pH 12 and extracted three times with t-butyl methyl ether, the combined extracts washed with brine, dried over sodium sulfate, filtered and evaporated.

Purification of the residue by flash-chromatography on silica gel with ethyl acetate as eluent provided 4-(3-benzyl-3H-imidazol-4-ylmethyl)-3,5-diethyl-1H-pyrazole as colourless viscous oil: MS (ISP): 295.3 ((M+H)$^+$.).

c) 3,5-Diethyl-4-(3H-imidazol-4-ylmethyl)-1H-pyrazole

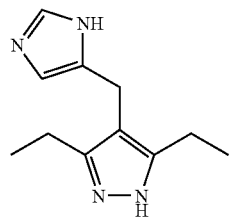

Hydrogenation of a solution of 110 mg (0.37 mmol) 4-(1-benzyl-1H-imidazol-2-ylmethyl)-3,5-diethyl-1H-pyrazole in 10 ml ethanol and 1 ml aqueous 2N HCl in presence of a catalytic mount of 10% Pd/C at 60° C. for 2 h provided after usual work-up pure 3,5-diethyl-4-(1H-imidazol-2-ylmethyl)-1H-pyrazole as colourless solid: MS (ISP): 205.2 ((M+H)$^+$.).

Example 56

3,5-Diethyl-4-(3H-imidazol-4-ylmethyl)-1-methyl-1H-pyrazole

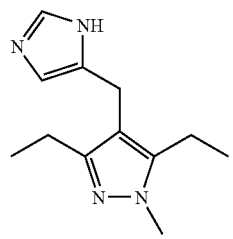

a) 4-(1-Benzyl-1H-imidazol-2-ylmethyl)-3,5-diethyl-1-methyl-1H-pyrazole or 4-(1-Benzyl-1H-imidazol-4-ylmethyl)-3,5-diethyl-1-methyl-1H-pyrazole

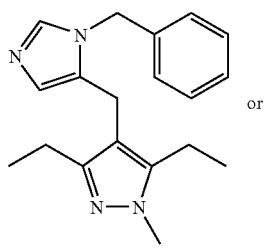

or

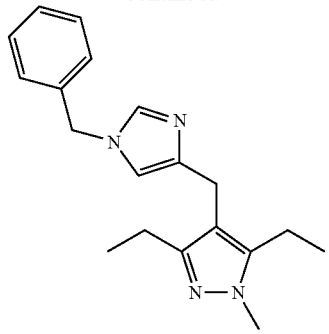

4-(1-Benzyl-1H-imidazol-2-ylmethyl)-3,5-diethyl-1-methyl-1H-pyrazole was prepared from 4-(3-benzyl-3H-imidazol-4-ylmethyl)-heptane-3,5-dione and methylhydrazine in analogy to Example 55 b): colourless solid; MS (ISP): 309.3 ((M+H)$^+$.).

b) 3,5-Diethyl-4-(3H-imidazol-4-ylmethyl)-1-methyl-1H-pyrazole

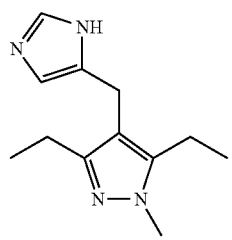

3,5-Diethyl-4-(3H-imidazol-4-ylmethyl)-1-methyl-1H-pyrazole was prepared from 4-(1-Benzyl-1H-imidazol-2-ylmethyl)-3,5-diethyl-1-methyl-1H-pyrazole in analogy to Example 55 c): colourless solid; MS (ISP): 219.0 ((M+H)$^+$.).

Example 57

4-(2-Ethyl-6-methyl-benzyl)-1H-imidazole

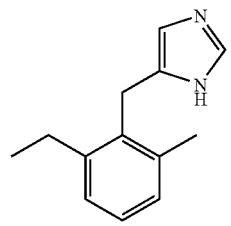

a) Butyl-[1-(2-chloro-6-fluoro-phenyl)-meth-(E)-ylidene]-amine

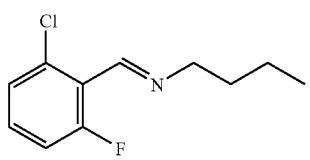

To a solution of 59.8 g (377 mmol) 2-chloro-6-fluorobenzaldehyde in 250 ml toluene were added 41.0 ml (415 mmol) N-butylamine and 1.44 g (7.54 mmol) p-toluenesulphonic acid. The mixture was heated at reflux for 5 h. After cooling to room temperature, the mixture was diluted with toluene and washed sequentially with aqueous sodium bicarbonate solution, water and saturated brine. The organic layer was dried over $Na_2SO_4$, filtered and concentrated in vacuo to afford 80.1 g (99% of the title compound as a dark brown oil which was used in the next step without further purification. MS (ISP): 216.2 ($[\{^{37}Cl\}M+H]^+$), 214.2 ($[\{^{35}Cl\}M+H]^+$).

b) Butyl-[1-(2-chloro-6-methyl-phenyl)-meth-(E)-ylidene]-amine

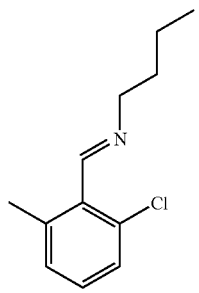

This compound was prepared using methodology described in *Synthesis* 1999, 2138-2144. To a solution of 7.00 g (32.8 mmol) butyl-[1-(2-chloro-6-fluoro-phenyl)-meth-(E)-ylidene]-amine in 70 ml tetrahydrofuran at 0° C. was added 0.41 g (3.28 mmol) manganese(II) chloride. 21.8 ml (65.5 mmol) of a 3 M solution of methylmagnesium chloride in tetrahydrofuran was then added dropwise while the temperature of the reaction mixture was maintained at 5-10° C. After the addition was complete, the reaction mixture was stirred for a further 30 minutes, during which time the temperature rose to 40° C. (exotherm). The reaction mixture was then quenched by dropwise addition of water and stirred for a further 30 minutes before being diluted with toluene. The mixture was then filtered and the organic phase of the filtrate was then washed with saturated brine. The phases were separated and the organic phase was dried over $Na_2SO_4$, filtered and concentrated in vacuo. The residue was resuspended in carbon tetrachloride and concentrated in vacuo again to afford 6.90 g (100%) of the title compound as a yellow oil which was used in the next step without further purification. MS (ISP): 212.1 ($[\{^{37}Cl\}M+H]^+$), 210.1 ($[\{^{35}Cl\}M+H]^+$).

c) 2-Ethyl-6-methyl-benzaldehyde

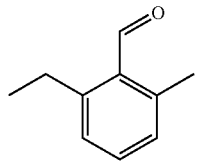

This compound was prepared using methodology described in *Synthesis* 1999, 2138-2144. To a solution of 3.20 g (15.3 mmol) butyl-[1-(2-chloro-6-methyl-phenyl)-meth-(E)-ylidene]-amine in 30 ml tetrahydrofuran at 0° C. was added 0.19 g (1.53 mmol) manganese(II) chloride. 15.3 ml (30.5 mmol) of a 2 M solution of ethylmagnesium chloride in diethyl ether was then added dropwise while the temperature of the reaction mixture was maintained at 5-10° C. After the addition was complete, the reaction mixture was stirred for a further 90 minutes, during which time the temperature rose to 50° C. (exotherm). The reaction mixture was then quenched by dropwise addition of water before being diluted with ethyl acetate. The mixture was then washed sequentially with water and with saturated brine. The phases were separated and the organic phase was dried over $Na_2SO_4$, filtered and concentrated in vacuo. The residue was purified by flash chromatography (silica gel, ethyl acetate/heptane gradient) to afford 1.88 g (83%) of the title compound as a yellow oil. $^1$H-NMR (CDCl$_3$): 1.26 (3H, t, CH$_3$), 2.60 (3H, s, CH$_3$), 2.98 (2H, q, CH$_2$), 7.09 (1H, d, ArH), 7.12 (1H, d, ArH), 7.35 (1H, dd, ArH), 10.6 (1H, s, CHO).

d) Rac-(2-Ethyl-6-methyl-phenyl)-(1-trityl-1H-imidazol-4-yl)-methanol

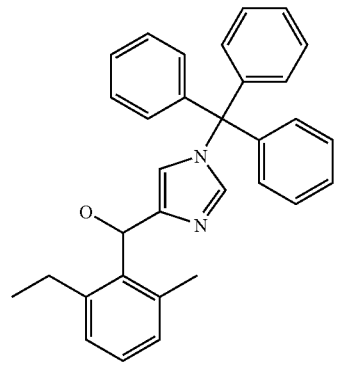

This compound was prepared using methodology described in *J. Org. Chem.* 1991, 56, 5739-5740. To a stirred suspension of 1.47 g (3.37 mmol) 4-iodo-tritylimidazole in 5 ml dichloromethane was added dropwise 1.12 ml (3.37 mmol) of a 3 M solution of ethylmagnesium bromide in diethyl ether at such a rate that the temperature of the reaction mixture did not rise above 28° C. The resulting solution of (1-trityl-1H-imidazol-4-yl)-magnesium halide was stirred at room temperature for 30 minutes, and then a solution of 0.50 g (3.37 mmol) 2-ethyl-6-methyl-benzaldehyde in 2 ml dichloromethane was added dropwise over 10 minutes. The reaction mixture was then stirred at room temperature for 5 h, before being quenched by dropwise addition of water and diluted with dichloromethane. The phases were separated and the organic phase was dried over $Na_2SO_4$, filtered and concentrated in vacuo to afford 1.40 g (90%) of the title compound as an off-white foam which was used in the next step without further purification.

e) 4-(2-Ethyl-6-methyl-benzyl)-1H-imidazole

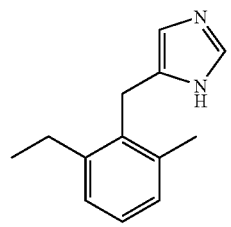

This compound was prepared using methodology described in *J. Chem. Soc., Perkin Trans.* 1, 2002, 1061-1066. To a stirred solution of 0.35 g (0.76 mmol) rac-(2-ethyl-6-methyl-phenyl)-(1-trityl-1H-imidazol-4-yl)-methanol in 5 ml dichloromethane were added dropwise 1.22 ml (7.63 mmol) triethylsilane and 0.69 ml (9.16 mmol) trifluoroacetic acid. The reaction mixture was stirred at room temperature for 16 hours, and then diluted with a 1:1 mixture of tetrahydrofuran and ethyl acetate. The mixture was washed sequentially with 2 N aqueous sodium hydroxide solution and saturated brine and then the organic phase was dried over Na$_2$SO$_4$, filtered and concentrated in vacuo. The residue was purified by flash chromatography (silica gel, methanol/dichloromethane gradient) to afford 40 mg (26%) of the title compound as a yellow crystalline solid. MS (ISP): 201.3 ([M+H]$^+$).

Example 58

4-(2-Cyclopropyl-6-ethyl-benzyl)-1H-imidazole

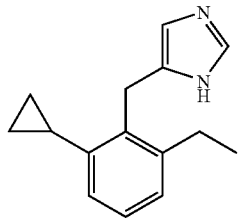

a) Butyl-[1-(2-chloro-6-ethyl-phenyl)-meth-(E)-ylidene]-amine

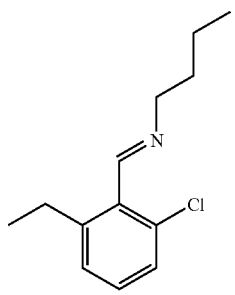

This compound was prepared using methodology described in *Synthesis* 1999, 2138-2144. To a solution of 21.2 g (99.2 mmol) butyl-[1-(2-chloro-6-fluoro-phenyl)-meth-(E)-ylidene]-amine in 150 ml tetrahydrofuran at 0° C. was added dropwise 38.0 ml (114 mmol) of a 3 M solution of ethylmagnesium bromide in ether at such a rate that the temperature of the reaction mixture was maintained below 20° C. After the addition was complete, the reaction mixture was stirred for a further 1 h at room temperature. The reaction mixture was then quenched by dropwise addition of water and diluted with ethyl acetate. The mixture was washed sequentially with water and with saturated brine, then the organic phase was dried over Na$_2$SO$_4$, filtered and concentrated in vacuo. The residue was resuspended in carbon tetrachloride and concentrated in vacuo again to afford 19.7 g (89%) of the title compound as a yellow oil which was used in the next step without further purification. MS (ISP): 226.3 ([{$^{37}$Cl}M+H]$^+$), 224.3 ([{$^{35}$Cl}M+H]$^+$). $^1$H NMR and MS analysis indicated that this material contained ca 13% of the by-product butyl-[1-(2-ethyl-6-fluoro-phenyl)-meth-(E)-ylidene]-amine. MS (ISP): 208.3 ([M+H]$^+$).

b) 2-Cyclopropyl-6-ethyl-benzaldehyde

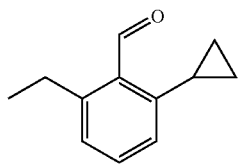

Prepared in analogy to Example 57(c) from butyl-[1-(2-chloro-6-ethyl-phenyl)-meth-(E)-ylidene]-amine, cyclopropylmagnesium bromide and manganese(II) chloride in tetrahydrofuran and ether followed by chromatography on silical gel. Yellow oil. $^1$H-NMR (CDCl$_3$): 0.74 (2H, m, CH$_2$), 1.02 (2H, m, CH$_2$), 1.25 (3H, t, CH$_3$), 2.40 (1H, m, CH), 2.98 (2H, q, CH$_2$), 7.04 (1H, d, ArH), 7.12 (1H, d, ArH), 7.36 (1H, dd, ArH), 10.9 (1H, s, CHO).

c) Rac-(2-Cyclopropyl-6-ethyl-phenyl)-(1-trityl-1H-imidazol-4-yl)-methanol

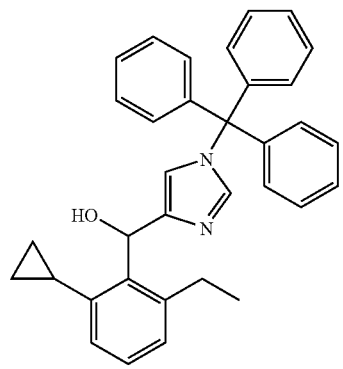

Prepared in analogy to Example 57(d) from 2-cyclopropyl-6-ethyl-benzaldehyde and in situ prepared (1-trityl-1H-imidazol-4-yl)-magnesium halide in dichloromethane.

d) 4-(2-Cyclopropyl-6-ethyl-benzyl)-1H-imidazole

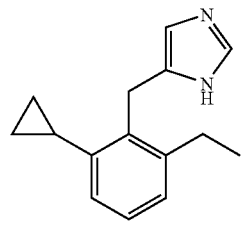

Prepared in analogy to Example 57(e) from rac-(2-cyclopropyl-6-ethyl-phenyl)-(1-trityl-1H-imidazol-4-yl)-methanol, triethylsilane and trifluoroacetic acid in dichloromethane. Off-white crystalline solid. MS (ISP): 227.4 ([M+H]$^+$).

Example 59

Rac-(2-Chloro-6-ethyl-phenyl)-(1H-imidazol-4-yl)-methanol

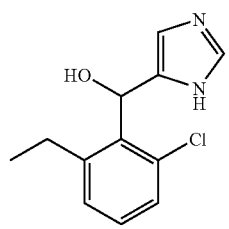

a) 2-Chloro-6-ethyl-benzaldehyde

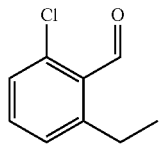

To a solution of 19.7 g (88.1 mmol) butyl-[1-(2-chloro-6-ethyl-phenyl)-meth-(E)-ylidene]-amine in 70 ml water at 0° C. was added dropwise 18.9 ml concentrated sulphuric acid. The mixture was then heated at reflux for 90 min before being cooled to room temperature and diluted with ethyl acetate. The mixture was then washed sequentially with water, saturated aqueous sodium bicarbonate solution, and saturated brine. The organic phase was dried over $Na_2SO_4$, filtered and concentrated in vacuo. The residue was purified by flash chromatography (silica gel, ethyl acetate/heptane 1:30) to afford 11.4 g (77%) of the title compound as a yellow oil. $^1$H-NMR (CDCl$_3$): 1.22 (3H, t, CH$_3$), 2.97 (2H, q, CH$_2$), 7.20 (1H, d, ArH), 7.30 (1H, d, ArH), 7.39 (1H, dd, ArH), 10.65 (1H, s, CHO).

b) Rac-(2-Chloro-6-ethyl-phenyl)-(1-trityl-1H-imidazol-4-yl)-methanol

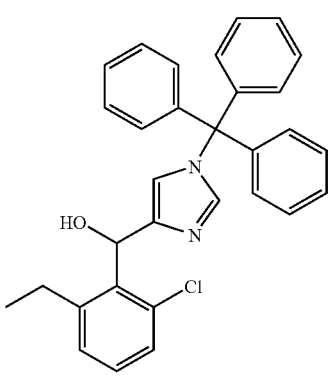

Prepared in analogy to Example 57(d) from 2-chloro-6-ethyl-benzaldehyde and in situ prepared (1-trityl-1H-imidazol-4-yl)-magnesium halide in dichloromethane. Yellow crystalline solid.

c) Rac-(2-Chloro-6-ethyl-phenyl)-(1H-imidazol-4-yl)-methanol

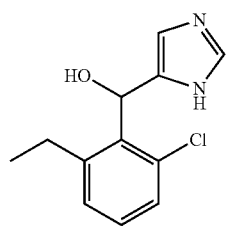

Prepared in analogy to Example 57(e) from rac-(2-chloro-6-ethyl-phenyl)-(1-trityl-1H-imidazol-4-yl)-methanol, triethylsilane and trifluoroacetic acid in dichloromethane at room temperature, with the title compound being obtained as a by-product resulting from deprotection of trityl group without concomitant reduction of the benzylic alcohol moiety. Yellow oil. MS (ISP): 238.9 ([{$^{37}$Cl}M+H]$^+$), 236.8 ([{$^{35}$Cl}M+H]$^+$).

Example 60

4-[3-(4-Chloro-phenoxy)-benzyl]-1H-imidazole

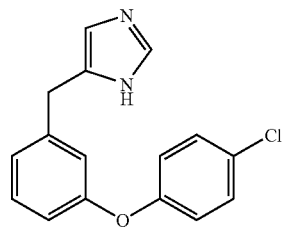

Prepared in analogy to Example 57(d)-(e) from 3-(4-chlorophenoxy)benzaldehyde and in situ prepared (1-trityl-1H-imidazol-4-yl)-magnesium halide in dichloromethane, then treatment with triethylsilane and trifluoroacetic acid in dichloromethane. White amorphous solid. MS (ISP): 287.2 ([{$^{37}$Cl}M+H]$^+$), 285.1 ([{$^{35}$Cl}M+H]$^+$).

Example 61

4-(2-Chloro-6-ethyl-benzyl)-1H-imidazole

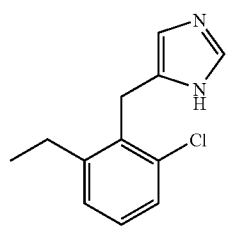

Prepared in analogy to Example 57(e) from rac-(2-chloro-6-ethyl-phenyl)-(1-trityl-1H-imidazol-4-yl)-methanol, triethylsilane and trifluoroacetic acid in dichloromethane, except that the reaction was carried out in a pressure tube at 70° C. for 16 h. White crystalline solid. MS (ISP): 223.3 ([{$^{37}$Cl}M+H]$^+$), 221.2 ([{$^{35}$Cl}M+H]$^+$).

Example 62

4-(3-Ethoxy-benzyl)-1H-imidazole

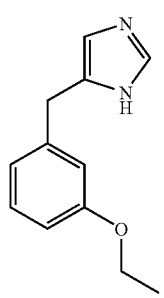

Prepared in analogy to Example 57(d)-(e) from 3-ethoxybenzaldehyde and in situ prepared (1-trityl-1H-imidazol-4-yl)-magnesium halide in dichloromethane, then treatment with triethylsilane and trifluoroacetic acid in dichloromethane in a pressure tube at 70° C. for 16 h. Yellow oil. MS (ISP): 203.4 ([M+H]$^+$).

Example 63

4-(2-Fluoro-5-methoxy-benzyl)-1H-imidazole

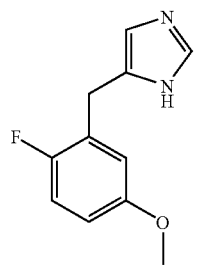

Prepared in analogy to Example 57(d)-(e) from 2-fluoro-5-methoxybenzaldehyde and in situ prepared (1-trityl-1H-imidazol-4-yl)-magnesium halide in dichloromethane, then treatment with triethylsilane and trifluoroacetic acid in dichloromethane in a pressure tube at 70° C. for 16 h. White crystalline solid. MS (ISP): 207.3 ([M+H]$^+$).

Example 64

4-[3-(1,1,2,2-Tetrafluoro-ethoxy)-benzyl]-1H-imidazole

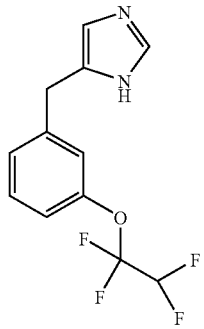

Prepared in analogy to Example 57(d)-(e) from 3-(1,1,2,2-tetrafluoroethoxy)benzaldehyde and in situ prepared (1-trityl-1H-imidazol-4-yl)-magnesium halide in dichloromethane, then treatment with triethylsilane and trifluoroacetic acid in dichloromethane in a pressure tube at 70° C. for 16 h. Yellow oil. MS (ISP): 275.3 ([M+H]$^+$).

Example 65

4-(3-Benzyloxy-benzyl)-1H-imidazole

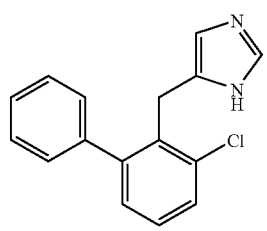

Prepared in analogy to Example 57(d)-(e) from 3-benzyloxybenzaldehyde and in situ prepared (1-trityl-1H-imidazol-4-yl)-magnesium halide in dichloromethane, then treatment with triethylsilane and trifluoroacetic acid in dichloromethane in a pressure tube at 70° C. for 16 h. Colourless oil. MS (ISP): 265.3 ([M+H]$^+$).

Example 66

4-(3-Chloro-biphenyl-2-ylmethyl)-1H-imidazole

Prepared in analogy to Example 57(c) from butyl-[1-(2-chloro-6-fluoro-phenyl)-meth-(E)-ylidene]-amine and phenylmagnesium chloride in tetrahydrofuran followed by chromatography on silical gel, then in analogy to Example 57(d)-(e) by treatment with in situ prepared (1-trityl-1H-imidazol-4-yl)-magnesium halide in dichloromethane, and then treatment with triethylsilane and trifluoroacetic acid in dichloromethane in a pressure tube at 70° C. for 16 h. Colourless oil. MS (ISP): 271.2 ([{$^{37}$Cl}M+H]$^+$), 269.3 ([{$^{35}$Cl}M+H]$^+$).

Example 67

4-Biphenyl-2-ylmethyl-1H-imidazole

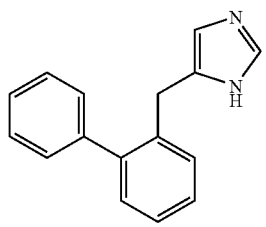

To a stirred solution of 50 mg (0.19 mmol) 4-(3-chloro-biphenyl-2-ylmethyl)-1H-imidazole in 40 ml methanol was added 40 mg of 10% palladium on charcoal and the mixture was then stirred for 16 h at room temperature under hydrogen at 0.6 bar excess pressure. The mixture was then filtered and the filtrate concentrated in vacuo to afford 25 mg (57%) of the title compound as a white crystalline solid. MS (ISP): 235.1 ([M+H]$^+$).

Example 68

4-(4'-Chloro-biphenyl-3-ylmethyl)-1H-imidazole

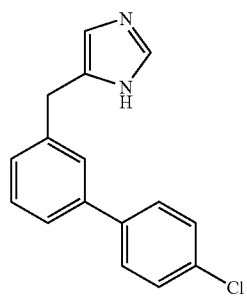

Prepared in analogy to Example 57(d)-(e) from 4'-chloro-biphenyl-3-carbaldehyde and in situ prepared (1-trityl-1H-imidazol-4-yl)-magnesium halide in dichloromethane, then treatment with triethylsilane and trifluoroacetic acid in dichloromethane in a pressure tube at 70° C. for 16 h. White crystalline solid. MS (ISP): 271.3 ([{$^{37}$Cl}M+H]$^+$), 269.3 ([{$^{35}$Cl}M+H]$^+$).

Example 69

4-(2,6-Diethyl-4-methoxy-benzyl)-1H-imidazole

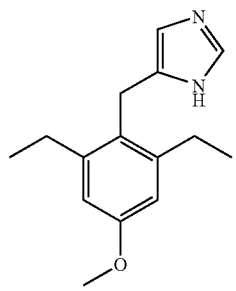

Prepared in analogy to Example 57(a)-(b) & (d)-(e) from 2,6-difluoro-4-methoxybenzaldehyde, N-butylamine and p-toluenesulphonic acid in toluene, then treatment with 3 equivalents of ethylmagnesium bromide and manganese(II) chloride in tetrahydrofuran and ether followed by chromatography on silical gel, then treatment with in situ prepared (1-trityl-1H-imidazol-4-yl)-magnesium halide in dichloromethane, and then treatment with triethylsilane and trifluoroacetic acid in dichloromethane in a pressure tube at 70° C. for 16 h. Light brown crystalline solid. MS (ISP): 245.3 ([M+H]$^+$).

Example 70

4-(2,6-Diethyl-3-methoxy-benzyl)-1H-imidazole

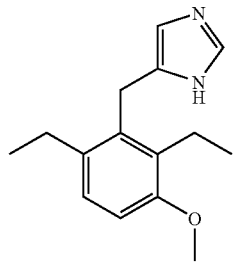

Prepared in analogy to Example 57(a)-(b) & (d)-(e) from 2,6-difluoro-3-methoxybenzaldehyde, N-butylamine and p-toluenesulphonic acid in toluene, then treatment with 3 equivalents of ethylmagnesium bromide and manganese(II) chloride in tetrahydrofuran and ether followed by chromatography on silical gel, then treatment with in situ prepared (1-trityl-1H-imidazol-4-yl)-magnesium halide in dichloromethane, and then treatment with triethylsilane and trifluo-

Example 71

4-Biphenyl-3-ylmethyl-1H-imidazole

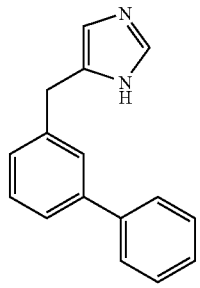

Prepared in analogy to Example 67 from 4-(4'-chloro-biphenyl-3-ylmethyl)-1H-imidazole, hydrogen and palladium in methanol. White crystalline solid. MS (ISP): 235.1 ([M+H]$^+$).

Example 72

4-(4-Ethoxy-2,6-diethyl-benzyl)-1H-imidazole

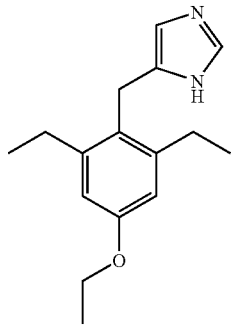

Prepared in analogy to Example 57(a)-(b) from 2,6-difluoro-4-methoxybenzaldehyde, N-butylamine and p-toluenesulphonic acid in toluene, then treatment with 3 equivalents of ethylmagnesium bromide and manganese(II) chloride in tetrahydrofuran and ether followed by chromatography on silical gel. MS (ISP): 193.3 ([M+H]$^+$).

b) 2,6-Diethyl-4-hydroxy-benzaldehyde

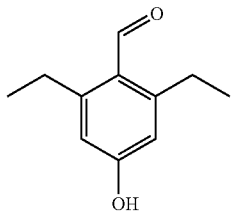

To a solution of 2.50 g (13.0 mmol) 2,6-diethyl-4-methoxy-benzaldehyde in 15 ml dichloromethane at −60° C. was added dropwise 26.0 ml (26.0 mmol) of a 1 M solution of boron tribromide in dichloromethane. After the addition was complete, the reaction mixture was allowed to warm to room temperature and then heated at reflux for 16 h. The reaction mixture was then cooled to room temperature and poured onto an ice-water mixture. The mixture was diluted with dichloromethane, the phases were separated, and the organic phase was dried over Na$_2$SO$_4$, filtered and concentrated in vacuo. The residue was resuspended in a 1:1 mixture of ethyl acetate and diethyl ether and extracted with 1 N aqueous sodium hydroxide solution. The phases were separated and the aqueous phase was acidified to pH 1 by addition of concentrated hydrochloric acid and then extracted with ethyl acetate. The phases were separated and the organic phase was washed with saturated brine, dried over Na$_2$SO$_4$, filtered and concentrated in vacuo to afford 1.48 g (64%) of the title compound as a brown crystalline solid. MS (ISP): 177.4 ([M−H]$^−$).

c) 4-Ethoxy-2,6-diethyl-benzaldehyde

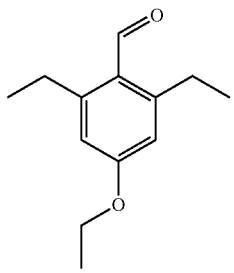

To a solution of 0.30 g (1.68 mmol) 2,6-diethyl-4-hydroxy-benzaldehyde in 8 ml N,N-dimethylformamide in a pressure tube were added 0.16 ml (2.02 mmol) iodoethane and 0.35 g (2.52 mmol) potassium carbonate. The tube was sealed and the reaction mixture was heated at 50° C. for 16 h. The reaction mixture was then cooled to room temperature, diluted with diethyl ether, and washed sequentially with water and saturated brine. The phases were separated, and the organic phase was dried over Na$_2$SO$_4$, filtered and concentrated in vacuo. The residue was purified by flash chromatography (silica gel, ethyl acetate/heptane 1:30) to afford 0.31 g (88%) of the title compound as a yellow oil. MS (ISP): 207.3 ([M+H]$^+$).

a) 2,6-Diethyl-4-methoxy-benzaldehyde

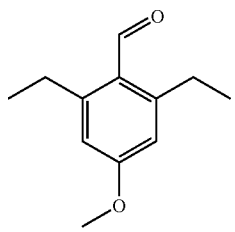

roacetic acid in dichloromethane in a pressure tube at 70° C. for 16 h. Light brown crystalline solid. MS (ISP): 245.4 ([M+H]$^+$).

d) Rac-(4-Ethoxy-2,6-diethyl-phenyl)-(1-trityl-1H-imidazol-4-yl)-methanol

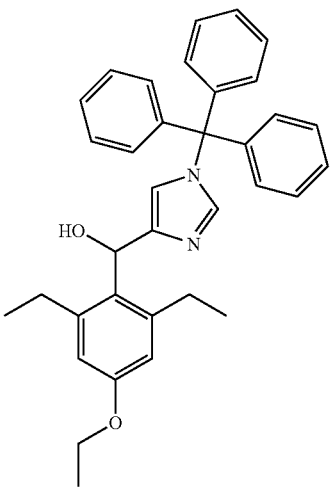

Prepared in analogy to Example 57(d) from 4-ethoxy-2,6-diethyl-benzaldehyde and in situ prepared (1-trityl-1H-imidazol-4-yl)-magnesium halide in dichloromethane. Yellow crystalline solid.

e) 4-(4-Ethoxy-2,6-diethyl-benzyl)-1H-imidazole

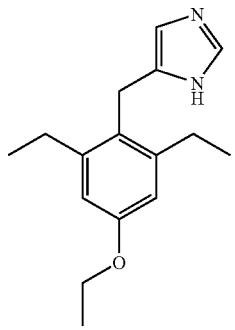

Prepared in analogy to Example 57(e) from rac-(4-ethoxy-2,6-diethyl-phenyl)-(1-trityl-1H-imidazol-4-yl)-methanol, triethylsilane and trifluoroacetic acid in dichloromethane in a pressure tube at 70° C. for 16 h. White crystalline solid. MS (ISP): 259.4 ([M+H]$^+$).

Example 73

4-(4-Benzyloxy-2,6-diethyl-benzyl)-1H-imidazole

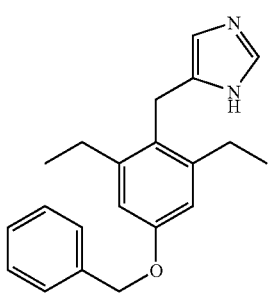

Prepared in analogy to Example 72(c)-(e) from 2,6-diethyl-4-hydroxy-benzaldehyde, benzyl bromide and potassium carbonate in N,N-dimethylformamide, then treatment with in situ prepared (1-trityl-1H-imidazol-4-yl)-magnesium halide in dichloromethane, and then treatment with triethylsilane and trifluoroacetic acid in dichloromethane in a pressure tube at 70° C. for 16 h. Amorphous white solid. MS (ISP): 321.1 ([M+H]$^+$).

Example 74

4-(3-Ethoxy-2,6-diethyl-benzyl)-1H-imidazole

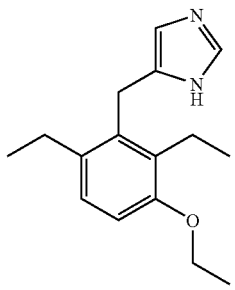

Prepared in analogy to Example 72(a)-(e) from 2,6-difluoro-3-methoxybenzaldehyde, N-butylamine and p-toluenesulphonic acid in toluene, then treatment with 3 equivalents of ethylmagnesium bromide and manganese(II) chloride in tetrahydrofuran and ether followed by chromatography on silical gel, then treatment with boron tribromide in dichloromethane, then treatment with iodoethane and potassium carbonate in N,N-dimethylformamide, then treatment with in situ prepared (1-trityl-1H-imidazol-4-yl)-magnesium halide in dichloromethane, and then treatment with triethylsilane and trifluoroacetic acid in dichloromethane in a pressure tube at 70° C. for 16 h. Amorphous white solid. MS (ISP): 259.3 ([M+H]$^+$).

Example 75

1,3,5-Triethyl-4-(3H-imidazol-4-ylmethyl)-1H-pyrazole

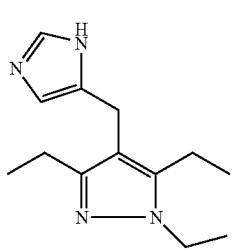

a) 4-(3-Benzyl-3H-imidazol-4-ylmethyl)-1,3,5-tri-ethyl-1H-pyrazole or 4-(1-Benzyl-1H-imidazol-4-ylmethyl)-1,3,5-triethyl-1H-pyrazole

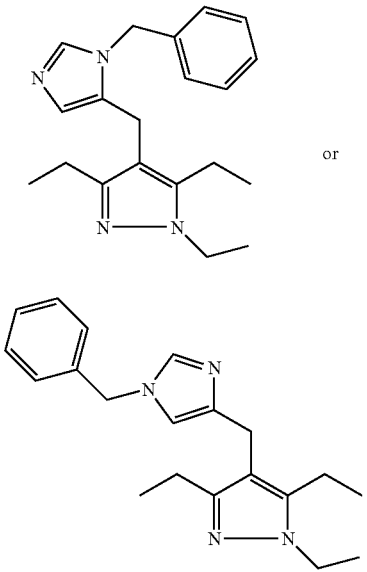

or 4-(3-Benzyl-3H-imidazol-4-ylmethyl)-1,3,5-triethyl-1H-pyrazole was prepared from 4-(3-benzyl-3H-imidazol-4-ylmethyl)-heptane-3,5-dione and ethylhydrazine in analogy to Example 55 b): off-white solid; MS (ISP): 323.3 ((M+H)⁺.).

b) 1,3,5-Triethyl-4-(3H-imidazol-4-ylmethyl)-1H-pyrazole

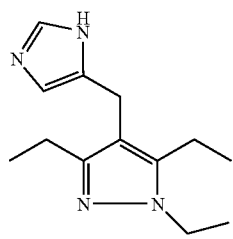

1,3,5-Triethyl-4-(3H-imidazol-4-ylmethyl)-1H-pyrazole was prepared from 4-(3-benzyl-3H-imidazol-4-ylmethyl)-1,3,5-triethyl-1H-pyrazole by debenzylation with sodium in liquid ammonia for 10 min. The blue reaction mixture was quenched by addition of solid ammonium chloride, the ammonia evaporated and the residue distributed between water and t-butyl methyl ether. The organic phase was washed with brine, dried over sodium sulfate, filtered and evaporated. 1,3,5-Triethyl-4-(3H-imidazol-4-ylmethyl)-1H-pyrazole was obtained as light yellow solid; MS (ISP): 233.0 ((M+H)⁺.).

Example 76

3,5-Diethyl-4-(3H-imidazol-4-ylmethyl)-1-isopropyl-1H-pyrazole

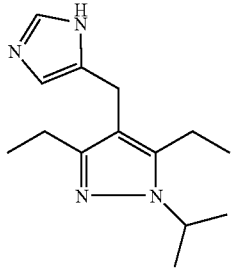

a) 4-(3-Benzyl-3H-imidazol-4-ylmethyl)-3,5-diethyl-1-isopropyl-1H-pyrazole or 4-(1-Benzyl-1H-imidazol-4-ylmethyl)-3,5-diethyl-1-isopropyl-1H-pyrazole

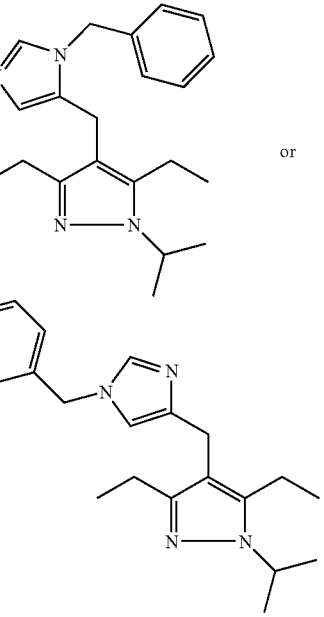

or 4-(3-Benzyl-3H-imidazol-4-ylmethyl)-3,5-diethyl-1-isopropyl-1H-pyrazole was prepared from 4-(3-benzyl-3H-imidazol-4-ylmethyl)-heptane-3,5-dione and isopropylhydrazine in analogy to Example 55 b): colourless solid; MS (ISP): 337.3 ((M+H)⁺.).

b) 3,5-Diethyl-4-(3H-imidazol-4-ylmethyl)-1-isopropyl-1H-pyrazole

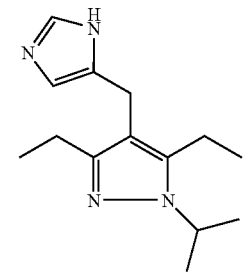

3,5-Diethyl-4-(3H-imidazol-4-ylmethyl)-1-isopropyl-1H-pyrazole was prepared from 4-(3-benzyl-3H-imidazol-4-ylmethyl)-3,5-diethyl-1-isopropyl-1H-pyrazole in analogy to Example 75 b): off-white solid; MS (ISP): 247.2 ((M+H)⁺.).

Example 77

3,5-Diethyl-4-(3H-imidazol-4-ylmethyl)-1-propyl-1H-pyrazole or tautomer

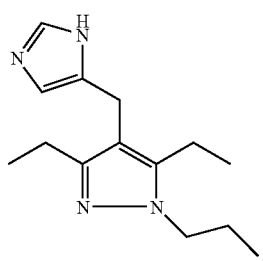

a) 4-(3-Benzyl-3H-imidazol-4-ylmethyl)-3,5-diethyl-1-propyl-1H-pyrazole or 4-(1-Benzyl-1H-imidazol-4-ylmethyl)-3,5-diethyl-1-propyl-1H-pyrazole

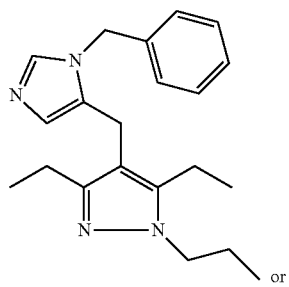

or

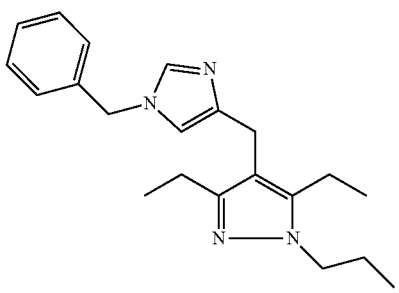

4-(3-Benzyl-3H-imidazol-4-ylmethyl)-3,5-diethyl-1-propyl-1H-pyrazole was prepared from 4-(3-benzyl-3H-imidazol-4-ylmethyl)-heptane-3,5-dione and propylhydrazine in analogy to Example 55 b): off-white solid; MS (ISP): 337.1 ((M+H)⁺.).

b) 3,5-Diethyl-4-(3H-imidazol-4-ylmethyl)-1-propyl-1H-pyrazole or tautomer

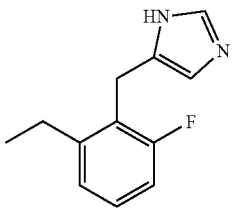

3,5-Diethyl-4-(3H-imidazol-4-ylmethyl)-1-propyl-1H-pyrazole was prepared from 4-(3-benzyl-3H-imidazol-4-yl-methyl)-3,5-diethyl-1-propyl-1H-pyrazole in analogy to Example 75 b): light yellow viscous oil; MS (ISP): 247.1 ((M+H)⁺.).

Example 78

4-(2-Ethyl-6-fluoro-benzyl)-1H-imidazole a) Butyl-[1-(2-ethyl-6-fluoro-phenyl)-meth-(E)-ylidene]-amine

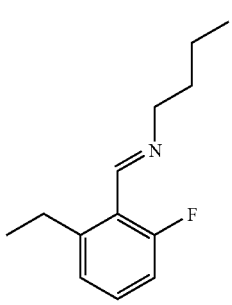

Prepared as described in Example 58(a) as by-product of reaction between butyl-[1-(2-chloro-6-fluoro-phenyl)-meth-(E)-ylidene]-amine and ethylmagnesium bromide in tetrahydrofuran and ether. MS (ISP): 208.3 ([M+H]⁺).

b) 2-Ethyl-6-fluoro-benzaldehyde

Prepared in analogy to Example 59(a) from butyl-[1-(2-ethyl-6-fluoro-phenyl)-meth-(E)-ylidene]-amine and aqueous sulphuric acid.

c) Rac-2-(tert-Butyl-dimethyl-silanyl)-4-[(2-ethyl-6-fluoro-phenyl)-hydroxy-methyl]-imidazole-1-sulfonic acid dimethylamide

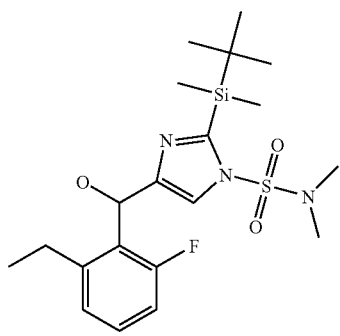

Prepared in analogy to Example 44(a) from 1-(dimethyl-sulfamoyl)-imidazole, butyl lithium and tert-butyldimethyl-silyl chloride in tetrahydrofuran to afford 2-(tert-butyl-dimethyl-silanyl)-imidazole-1-sulfonic acid dimethylamide, then treatment of this with butyl lithium and 2-ethyl-6-fluoro-benzaldehyde in tetrahydrofuran. White crystalline solid. MS (ISP): 442.1 ([M+H]$^+$).

d) 4-(2-Ethyl-6-fluoro-benzyl)-1H-imidazole

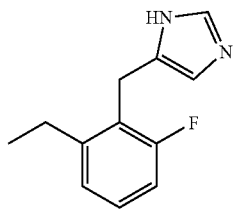

Prepared in analogy to Example 57(e) from rac-2-(tert-butyl-dimethyl-silanyl)-4-[(2-ethyl-6-fluoro-phenyl)-hydroxy-methyl]-imidazole-1-sulfonic acid dimethylamide, triethylsilane and trifluoroacetic acid in dichloromethane in a pressure tube at 100° C. for 16 h. White crystalline solid. MS (ISP): 205.3 ([M+H]$^+$).

Example 79

4-(2,6-Diethyl-4-phenoxy-benzyl)-1H-imidazole

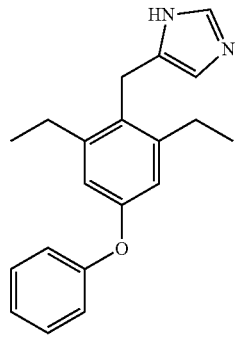

a) 2,6-Diethyl-4-phenoxy-benzaldehyde

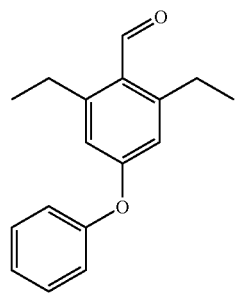

To a solution of 1.50 g (8.42 mmol) 2,6-diethyl-4-hydroxy-benzaldehyde in 60 ml dichloromethane were added 1.64 g (13.5 mmol) phenylboronic acid, 2.29 g (12.6 mmol) copper (II) acetate, 30 g 4 Å molecular sieves and 4.06 ml (50.5 mmol) pyridine. The reaction mixture was stirred at room temperature for 72 h and then filtered through celite. The filtrate was extracted with 1 N aqueous hydrochloric acid, the phases were separated, and the organic phase was dried over Na$_2$SO$_4$, filtered and concentrated in vacuo. The residue was purified by flash chromatography (silica gel, ethyl acetate/heptane gradient) to afford 1.64 g (77%) of the title compound as a yellow oil. $^1$H-NMR (CDCl$_3$): 1.22 (6H, t, CH$_3$), 2.95 (4H, q, CH$_2$), 6.69 (2H, s, ArH), 7.08 (2H, d, ArH), 7.20 (1H, t, ArH), 7.39 (2H, dd, ArH), 10.5 (1H, s, CHO).

b) Rac-2-(tert-Butyl-dimethyl-silanyl)-4-[(2,6-diethyl-4-phenoxy-phenyl)-hydroxy-methyl]-imidazole-1-sulfonic acid dimethylamide

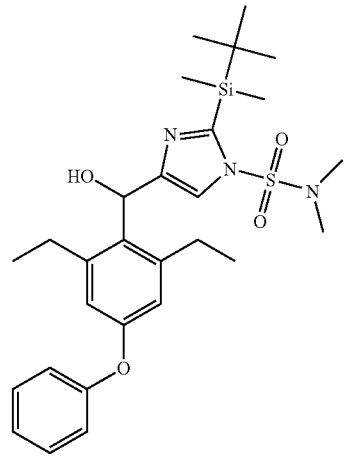

Prepared in analogy to Example 44(a) from 1-(dimethyl-sulfamoyl)-imidazole, butyl lithium and tert-butyldimethyl-silyl chloride in tetrahydrofuran to afford 2-(tert-butyl-dimethyl-silanyl)-imidazole-1-sulfonic acid dimethylamide, then treatment of this with butyl lithium and 2,6-diethyl-4-phenoxy-benzaldehyde in tetrahydrofuran. White crystalline solid. MS (ISP): 544.5 ([M+H]$^+$).

c) 4-(2,6-Diethyl-4-phenoxy-benzyl)-1H-imidazole

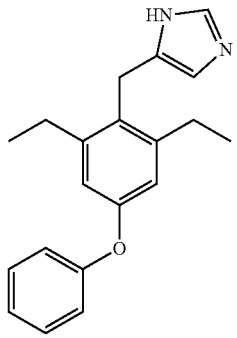

Prepared in analogy to Example 57(e) from rac-2-(tert-butyl-dimethyl-silanyl)-4-[(2,6-diethyl-4-phenoxy-phenyl)-hydroxy-methyl]-imidazole-1-sulfonic acid dimethylamide, triethylsilane and trifluoroacetic acid in dichloromethane in a pressure tube at 100° C. for 16 h. White crystalline solid. MS (ISP): 307.3 ([M+H]$^+$).

Example 80

4-(2,6-Diethyl-3-phenoxy-benzyl)-1H-imidazole

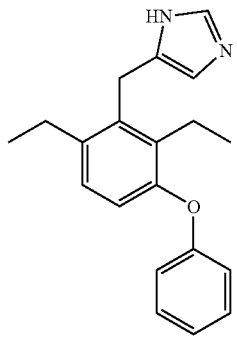

Prepared in analogy to Example 72(a)-(b) from 2,6-difluoro-3-methoxybenzaldehyde, N-butylamine and p-toluenesulphonic acid in toluene, then treatment with 3 equivalents of ethylmagnesium bromide and manganese(II) chloride in tetrahydrofuran and ether followed by chromatography on silical gel, then treatment with boron tribromide in dichloromethane, then in analogy to Example 79(a)-(c) by treatment with phenylboronic acid, copper(II) acetate, 4 Å molecular sieves and pyridine in dichloromethane, then treatment with in situ prepared 2-(tert-butyl-dimethyl-silanyl)-imidazole-1-sulfonic acid dimethylamide and butyl lithium in tetrahydrofuran, and then treatment with triethylsilane and trifluoroacetic acid in dichloromethane in a pressure tube at 100° C. for 16 h. White crystalline solid. MS (ISP): 307.4 ([M+H]$^+$).

The invention claimed is:

1. A compound of formula I

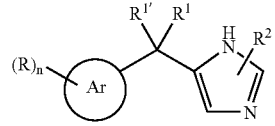

wherein
R is benzyloxy,
Ar is aryl or heteroaryl, selected from the group consisting of phenyl, naphthyl, pyridinyl, benzofuranyl, dihydrobenzofuranyl and pyrazolyl;
$R^1$ and $R^{1'}$ are each independently hydrogen,
hydroxy,
lower alkyl,
lower alkoxy, or
phenyl or benzyl, each of which is optionally substituted by halogen;
$R^2$ is hydrogen or lower alkyl; and
n is 1;
or a pharmaceutically active salt, racemic mixture, enantiomer, optical isomer or tautomeric form thereof.

2. A pharmaceutical composition comprising a therapeutically effective amount of a compound of formula I

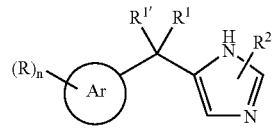

wherein
R is benzyloxy,
Ar is aryl or heteroaryl, selected from the group consisting of phenyl, naphthyl, pyridinyl, benzofuranyl, dihydrobenzofuranyl and pyrazolyl;
$R^1$ and $R^{1'}$ are each independently hydrogen,
hydroxy,
lower alkyl,
lower alkoxy, or
phenyl or benzyl, each of which is optionally substituted by halogen;
$R^2$ is hydrogen or lower alkyl; and
n is 1;
or a pharmaceutically active salt, racemic mixture, enantiomer, optical isomer or tautomeric form thereof.

3. The compound 4-(4-benzyloxy-2,6-diethyl-benzyl)-1H-imidazole.

* * * * *